US010398752B2

(12) United States Patent
Hong et al.

(10) Patent No.: US 10,398,752 B2
(45) Date of Patent: Sep. 3, 2019

(54) DERMATOPONTIN AS A THERAPEUTIC FOR METABOLIC DISORDERS

(71) Applicant: AGENCY FOR SCIENCE, TECHNOLOGY AND RESEARCH, Singapore (SG)

(72) Inventors: Wanjin Hong, Singapore (SG); Shixiong Tan, Singapore (SG); Weiping Han, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/550,768

(22) PCT Filed: Feb. 11, 2016

(86) PCT No.: PCT/SG2016/050066
§ 371 (c)(1),
(2) Date: Aug. 11, 2017

(87) PCT Pub. No.: WO2016/130085
PCT Pub. Date: Aug. 18, 2016

(65) Prior Publication Data
US 2018/0036371 A1 Feb. 8, 2018

(30) Foreign Application Priority Data

Feb. 11, 2015 (SG) .......................... 10201501053Q

(51) Int. Cl.
*A61K 38/17* (2006.01)
*G01N 33/68* (2006.01)
*A61K 38/16* (2006.01)

(52) U.S. Cl.
CPC .......... *A61K 38/1709* (2013.01); *A61K 38/16* (2013.01); *G01N 33/6893* (2013.01); *G01N 2800/02* (2013.01); *G01N 2800/04* (2013.01); *G01N 2800/042* (2013.01)

(58) Field of Classification Search
CPC .... A61K 38/1709; A61K 38/00; G01N 38/16; G01N 38/1709; G01N 2800/02; G01N 2800/04; G01N 33/6893
See application file for complete search history.

(56) References Cited

FOREIGN PATENT DOCUMENTS

| CN | 101782583 A | 7/2010 |
|---|---|---|
| JP | 2003-250556 A | 9/2003 |
| JP | 2006-141233 | 6/2006 |
| WO | WO 2003/023066 A1 | 3/2003 |
| WO | WO 2004/092416 A1 | 10/2004 |
| WO | WO 2008/042510 A2 | 4/2008 |
| WO | WO 2013/158230 A1 | 10/2013 |
| WO | WO 2015/176066 A2 | 11/2015 |

OTHER PUBLICATIONS

Natalie Olsen, Nutrition and Metabolism Disorders, accessed on May 9, 2018.*
IP Office of Singapore; Notification of Transmittal of the International Search Report and the Written Opinion of the International Searching Authority, or the Declaration for counterpart International Application No. PCT/SG2016/050066 containing International Search Report and Written Opinion, dated Mar. 28, 2016, 14 pages.
Boström, P, et al., "A PGC1α-Dependent Myokine That Drives Brown-Fat-Like Development of White Fat and Thermogenesis," *Nature*, Dec. 14, 2012, vol. 481(7382): pp. 463-468 (19 pages).
Chen L. et al., "The Worldwide Epidemiology of Type 2 Diabetes Mellitus-present and Future Perspectives," *Nat Rev Endocrinol*; Apr. 2012, vol. 8, Macmillian Publ. Ltd., pp. 228-236.
Elam, M.B., et al., "Hepatic Gene Expression in Morbidly Obese Women: Implications for Disease Susceptibility," *Obesity (Silver Spring)*, Mar. 5, 2009, vol. 17, No. 8, pp. 1563-1573.
Kato, A., et al., "Dermatopontin Interacts with Fibronectin, Promotes Fibronectin Fibril Formation, and Enhances Cell Adhesion," J. Biol Chem, Apr. 29, 2011, vol. 286: pp. 14861-14869 (10 pages).
Kharitonenkov, A, et al., "FGF-21 as a novel metabolic regulator," J Clin Invest (Jun. 2005) vol. 115, No. 6, pp. 1627-1635 (9 pages).
Liu, X., et al., "Dermatopontin promotes adhesion, spreading and migration of cardiac fibroblasts in vitro," *Matrix Biol* (2013) vol. 32: Elsevier B.V., pp. 23-31 (9 pages).
Okamoto, O., et al., "Dermatopontin Promotes Epidermal Keratinocyte Adhesion via α3β Integrin and a Proteoglycan Receptor," *Biochemistry* Nov. 24, 2009, (2010) vol. 49, No. 1, American Chemical Society, pp. 147-155 (9 pages).
Okamoto, O., et al., Extracellular Matrix 22-kDa Protein Interacts with Decorin Core Protein and Is Expressed in Cutaneous Fibrosis, *J Biochem* (1996) vol. 119: 106-114 (9 pages).
Okamoto, O., et al., "Dermatopontin Interacts With Transforming Growth Factor β and Enhances Its Biological Activity," *Biochem J.* (Feb. 1, 1999) vol. 337, pp. 537-541 (5 pages).

(Continued)

Primary Examiner — James H Alstrum-Acevedo
Assistant Examiner — Erinne R Dabkowski
(74) Attorney, Agent, or Firm — Womble Bond Dickinson (US) LLP

(57) ABSTRACT

The present disclosure describes to a method of treating a metabolic disease in a subject, wherein the method comprises administration of dermatopontin to a subject, wherein the dermatopontin is recombinant dermatopontin and the metabolic disease is selected from a group consisting of weight gain, diet-induced weight gain, obesity, morbid obesity, metabolic syndrome, glucose homeostasis, insulin resistance, type I diabetes, type if diabetes and cardiovascular disease. Disclosed herein is also a method of determining or making a prognosis of a subject's susceptibility to metabolic diseases and obesity, the method comprising measuring the level of circulating dermatopontin in a sample obtained from a subject; and comparing the level of circulating dermatopontin obtained with the level of dermatopontin previously determined in a control; and determining the susceptibility of the subject to metabolic disease and obesity based on the difference between the level of circulating dermatopontin and the level of dermatopontin in the control.

12 Claims, 10 Drawing Sheets

Specification includes a Sequence Listing.

(56) References Cited

OTHER PUBLICATIONS

Petrovic, N., et al., "Chronic Peroxisome Proliferator-activated Receptor γ (PPARγ) Activation of Epididymally Derived White Adipocyte Cultures Reveals a Population of Thermogenically Competent, UCP1-Containing Adipocytes Molecularly Distinct From Classic Brown Adipocytes," *J Biol Chem* (Mar. 5, 2010) vol. 285, No. 10, pp. 7153-7164 (13 pages).

Phillips, S.A., et al, "Mechanisms of Adiponectin Regulation and Use as a Pharmacological Target," *Curr Opin Pharmacol* (2010) vol. 10, pp. 676-683 (8 pages).

Schulz, T.J., et al., "Identification of Inducible Brown Adipocyte Progenitors Residing in Skeletal Muscle and White Fat," (Jan. 4, 2011) *Proc Natl Acad Sci USA*, vol. 10, No. 1, pp. 143-148 (6 pages).

Superti-Furga, A., et al., "Complementary DNA Sequence and Chromosomal Mapping of a Human Proteoglycan-Binding Cell-Adhesion Protein (Dermatopontin)," *Genomics* (1993) vol. 17, pp. 463-467 (5 pages).

Takeda, U., et al., "Targeted Disruption of Dermatopontin Causes Abnormal Collagen Fibrillogenesis," *J Invest Dermatol* (Sep. 3, 2002) vol. 119, No. 3, pp. 678-683 (6 pages).

Urs, S., et al., "Gene Expression Profiling in Human Preadipocytes and Adipocytes by Microarray Analysis," *J Nutr* (2004) vol. 134, No. 4, pp. 762-770 (9 pages).

Extended European Search Report, dated Aug. 27, 2018, for European Application No. 16749546.4.

\* cited by examiner

SEQUENCE LISTING

<160> NUMBER OF SEQ ID NOS: 12

<210> SEQ ID NO 1
<211> LENGTH: 201
<212> TYPE: PRT
<213> ORGANISM: artificial
<220> FEATURE:
<223> OTHER INFORMATION: Recombinant dermatopontin (human)

<400> SEQUENCE: 1

Met Asp Leu Ser Leu Leu Trp Val Leu Leu Pro Leu Val Thr Met Ala
1               5                   10                  15

Trp Gly Gln Tyr Gly Asp Tyr Gly Tyr Pro Tyr Gln Gln Tyr His Asp
                20                  25                  30

Tyr Ser Asp Asp Gly Trp Val Asn Leu Asn Arg Gln Gly Phe Ser Tyr
            35                  40                  45

Gln Cys Pro Gln Gly Gln Val Ile Val Ala Val Arg Ser Ile Phe Ser
    50                  55                  60

Lys Lys Glu Gly Ser Asp Arg Gln Trp Asn Tyr Ala Cys Met Pro Thr
65                  70                  75                  80

Pro Gln Ser Leu Gly Glu Pro Thr Glu Cys Trp Trp Glu Glu Ile Asn
                85                  90                  95

Arg Ala Gly Met Glu Trp Tyr Gln Thr Cys Ser Asn Asn Gly Leu Val
                100                 105                 110

Ala Gly Phe Gln Ser Arg Tyr Phe Glu Ser Val Leu Asp Arg Glu Trp
            115                 120                 125

Gln Phe Tyr Cys Cys Arg Tyr Ser Lys Arg Cys Pro Tyr Ser Cys Trp
    130                 135                 140

Leu Thr Thr Glu Tyr Pro Gly His Tyr Gly Glu Met Asp Met Ile
145                 150                 155                 160

Ser Tyr Asn Tyr Asp Tyr Tyr Ile Arg Gly Ala Thr Thr Thr Phe Ser
                165                 170                 175

Ala Val Glu Arg Asp Arg Gln Trp Lys Phe Ile Met Cys Arg Met Thr
            180                 185                 190

Glu Tyr Asp Cys Glu Phe Ala Asn Val
            195                 200

<210> SEQ ID NO 2
<211> LENGTH: 201
<212> TYPE: PRT
<213> ORGANISM: artificial
<220> FEATURE:
<223> OTHER INFORMATION: Recombinant dermatopontin (bovine)

<400> SEQUENCE: 2

Met Asp Leu Thr Leu Leu Trp Val Leu Leu Pro Leu Val Thr Val Ala
1               5                   10                  15

Trp Gly Gln Tyr Gly Asp Tyr Gly Tyr Ser Tyr His Gln Tyr His Asp
                20                  25                  30

Tyr Ser Asp Asp Gly Trp Val Asn Leu Asn Arg Gln Gly Phe Ser Tyr
            35                  40                  45

Gln Cys Pro His Gly Gln Val Val Ala Val Arg Ser Ile Phe Asn
    50                  55                  60

Lys Lys Glu Gly Ser Asp Arg Gln Trp Asn Tyr Ala Cys Met Pro Thr
65                  70                  75                  80

Pro Gln Ser Leu Gly Glu Pro Thr Glu Cys Trp Trp Glu Glu Ile Asn
                85                  90                  95

```
Arg Ala Gly Met Glu Trp Tyr Gln Thr Cys Ser Asn Asn Gly Leu Val
            100                 105                 110

Ala Gly Phe Gln Ser Arg Tyr Phe Glu Ser Val Leu Asp Arg Glu Trp
        115                 120                 125

Gln Phe Tyr Cys Cys Arg Tyr Ser Lys Arg Cys Pro Tyr Ser Cys Trp
    130                 135                 140

Leu Thr Thr Glu Tyr Pro Gly His Tyr Gly Glu Met Asp Met Ile
145                 150                 155                 160

Ser Tyr Asn Tyr Asp Tyr Tyr Met Arg Gly Ala Thr Thr Phe Ser
                165                 170                 175

Ala Val Glu Arg Asp Arg Gln Trp Lys Phe Ile Met Cys Arg Met Thr
                180                 185                 190

Asp Tyr Asp Cys Glu Phe Ala Asn Val
        195                 200

<210> SEQ ID NO 3
<211> LENGTH: 201
<212> TYPE: PRT
<213> ORGANISM: artificial
<220> FEATURE:
<223> OTHER INFORMATION: Recombinant dermatopontin (murine)

<400> SEQUENCE: 3

Met Asp Leu Thr Leu Leu Trp Val Leu Leu Pro Leu Val Thr Thr Ala
1               5                   10                  15

Trp Gly Gln Tyr Gly Gly Tyr Gly Tyr Pro Tyr Gln Asn Tyr Gln Asp
                20                  25                  30

Tyr Gly Asp Asp Gly Trp Val Asn Leu Asn Arg Gln Gly Phe Ser Tyr
            35                  40                  45

Gln Cys Pro His Gly Gln Val Val Ala Val Arg Ser Ile Phe Ser
    50                  55                  60

Lys Lys Glu Gly Ser Asp Arg Gln Trp Asn Tyr Ala Cys Met Pro Thr
65                  70                  75                  80

Pro Gln Ser Leu Gly Glu Pro Thr Glu Cys Trp Trp Glu Glu Ile Asn
                85                  90                  95

Arg Ala Gly Met Glu Trp Tyr Gln Lys Cys Ser Asn Asn Gly Leu Val
            100                 105                 110

Ala Gly Phe Gln Ser Arg Tyr Phe Glu Ser Val Leu Asp Arg Glu Trp
        115                 120                 125

Gln Phe Tyr Cys Cys Arg Tyr Ser Lys Arg Cys Pro Tyr Ser Cys Trp
    130                 135                 140

Met Thr Thr Glu Tyr Pro Ser His Tyr Gly Glu Asp Met Asp Met Ile
145                 150                 155                 160

Ser Tyr Asp Tyr Asp Phe Tyr Met Arg Gly Ala Thr Thr Phe Ser
                165                 170                 175

Ala Val Glu Arg Asp Arg Gln Trp Lys Phe Ile Met Cys Arg Met Thr
                180                 185                 190

Asp Tyr Asp Cys Glu Phe Glu Asn Val
        195                 200

<210> SEQ ID NO 4
<211> LENGTH: 183
<212> TYPE: PRT
<213> ORGANISM: artificial
<220> FEATURE:
<223> OTHER INFORMATION: Recombinant dermatopontin (porcine)
```

<400> SEQUENCE: 4

```
Gln Tyr Gly Asp Tyr Gly Tyr Pro Tyr Gln Gln Tyr His Asp Tyr Ser
1               5                   10                  15
Asp Asp Gly Trp Val Asn Leu Asn Arg Gln Gly Phe Ser Tyr Gln Cys
            20                  25                  30
Pro His Gly Gln Val Val Val Ala Val Arg Ser Ile Phe Asn Lys Lys
        35                  40                  45
Glu Gly Ser Asp Arg Gln Trp Asn Tyr Ala Cys Met Pro Thr Pro Gln
    50                  55                  60
Ser Leu Gly Glu Pro Ser Glu Cys Trp Trp Glu Ile Asn Arg Ala
65              70                  75                  80
Gly Met Glu Trp Tyr Gln Thr Cys Ser Asn Asn Gly Leu Val Ala Gly
                85                  90                  95
Phe Gln Ser Arg Tyr Phe Glu Ser Val Leu Asp Arg Glu Trp Gln Phe
            100                 105                 110
Tyr Cys Cys Arg Tyr Ser Lys Arg Cys Pro Tyr Ser Cys Trp Met Thr
        115                 120                 125
Thr Glu Tyr Pro Gly His Tyr Gly Glu Glu Met Asp Met Ile Ser Tyr
    130                 135                 140
Asn Tyr Asp Tyr Tyr Met Arg Gly Ala Thr Thr Thr Phe Ser Ala Val
145                 150                 155                 160
Glu Arg Asp Arg Gln Trp Lys Phe Ile Met Cys Arg Met Thr Asp Tyr
                165                 170                 175
Asp Cys Glu Phe Ala Asn Val
            180
```

<210> SEQ ID NO 5
<211> LENGTH: 606
<212> TYPE: DNA
<213> ORGANISM: artificial
<220> FEATURE:
<223> OTHER INFORMATION: Human dermatopontin (DPT) nucleic acid sequence used to generate recombinant DPT constructs

<400> SEQUENCE: 5

```
atggacctca gtcttctctg ggtacttctg cccctagtca ccatggcctg gggccagtat      60
ggcgattatg gatacccata ccagcagtat catgactaca gcgatgatgg gtgggtgaat     120
ttgaaccggc aaggcttcag ctaccagtgt ccccaggggc aggtgatagt ggccgtgagg     180
agcatcttca gcaagaagga aggttctgac agacaatgga actacgcctg catgcccacg     240
ccacagagcc tcggggaacc cacggagtgc tggtgggagg agatcaacag ggctggcatg     300
gaatggtacc agacgtgctc caacaatggg ctggtggcag gattccagag ccgctacttc     360
gagtcagtgc tggatcggga gtggcagttt tactgttgtc gctacagcaa gaggtgccca     420
tattcctgct ggctaacaat agaatatcca ggtcactatg gtgaggaaat ggacatgatt     480
tcctacaatt atgattacta tatccgagga gcaacaacca ctttctctgc agtggaaagg     540
gatcgccagt ggaagttcat aatgtgccgg atgactgaat acgactgtga atttgcaaat     600
gtttag                                                               606
```

<210> SEQ ID NO 6
<211> LENGTH: 18
<212> TYPE: PRT
<213> ORGANISM: artificial
<220> FEATURE:
<223> OTHER INFORMATION: Conserved N-terminal secretory sequence (human)

```
<400> SEQUENCE: 6

Met Asp Leu Ser Leu Leu Trp Val Leu Leu Pro Leu Val Thr Met Ala
1               5                   10                  15

Trp Gly

<210> SEQ ID NO 7
<211> LENGTH: 18
<212> TYPE: PRT
<213> ORGANISM: artificial
<220> FEATURE:
<223> OTHER INFORMATION: Conserved N-terminal secretory sequence
      (bovine)

<400> SEQUENCE: 7

Met Asp Leu Thr Leu Leu Trp Val Leu Leu Pro Leu Val Thr Val Ala
1               5                   10                  15

Trp Gly

<210> SEQ ID NO 8
<211> LENGTH: 18
<212> TYPE: PRT
<213> ORGANISM: artificial
<220> FEATURE:
<223> OTHER INFORMATION: Conserved N-terminal secretory sequence
      (murine)

<400> SEQUENCE: 8

Met Asp Leu Thr Leu Leu Trp Val Leu Leu Pro Leu Val Thr Thr Ala
1               5                   10                  15

Trp Gly

<210> SEQ ID NO 9
<211> LENGTH: 20
<212> TYPE: PRT
<213> ORGANISM: artificial
<220> FEATURE:
<223> OTHER INFORMATION: Nuclear localisation sequence of nucleoplasmin

<400> SEQUENCE: 9

Ala Val Lys Arg Pro Ala Ala Thr Lys Lys Ala Gly Gln Ala Lys Lys
1               5                   10                  15

Lys Lys Leu Asp
            20

<210> SEQ ID NO 10
<211> LENGTH: 9
<212> TYPE: PRT
<213> ORGANISM: artificial
<220> FEATURE:
<223> OTHER INFORMATION: Nuclear localisation sequence of c-myc

<400> SEQUENCE: 10

Pro Ala Ala Lys Arg Val Lys Leu Asp
1               5

<210> SEQ ID NO 11
<211> LENGTH: 624
<212> TYPE: DNA
<213> ORGANISM: artificial
<220> FEATURE:
<223> OTHER INFORMATION: His-tagged recombinant dermatopontin (rDPT-His)
```

<400> SEQUENCE: 11

```
atggacctca gtcttctctg ggtacttctg cccctagtca ccatggcctg gggccagtat      60
ggcgattatg gatacccata ccagcagtat catgactaca gcgatgatgg gtgggtgaat     120
ttgaaccggc aaggcttcag ctaccagtgt ccccaggggc aggtgatagt ggccgtgagg     180
agcatcttca gcaagaagga aggttctgac agacaatgga actacgcctg catgcccacg     240
ccacagagcc tcggggaacc cacggagtgc tggtgggagg agatcaacag gctggcatg      300
gaatggtacc agacgtgctc caacaatggg ctggtggcag gattccagag ccgctacttc     360
gagtcagtgc tggatcggga gtggcagttt tactgttgtc gctacagcaa gaggtgccca     420
tattcctgct ggctaacaat agaatatcca ggtcactatg gtgaggaaat ggacatgatt     480
tcctacaatt atgattacta tatccgagga gcaacaacca ctttctctgc agtggaaagg     540
gatcgccagt ggaagttcat aatgtgccgg atgactgaat cgactgtga atttgcaaat     600
gttcatcatc atcatcatca ttga                                           624
```

<210> SEQ ID NO 12
<211> LENGTH: 207
<212> TYPE: PRT
<213> ORGANISM: artificial
<220> FEATURE:
<223> OTHER INFORMATION: His-tagged recombinant dermatopontin (rDPT-His)

<400> SEQUENCE: 12

```
Met Asp Leu Ser Leu Leu Trp Val Leu Leu Pro Leu Val Thr Met Ala
1               5                   10                  15

Trp Gly Gln Tyr Gly Asp Tyr Gly Tyr Pro Tyr Gln Gln Tyr His Asp
            20                  25                  30

Tyr Ser Asp Asp Gly Trp Val Asn Leu Asn Arg Gln Gly Phe Ser Tyr
        35                  40                  45

Gln Cys Pro Gln Gly Gln Val Ile Val Ala Val Arg Ser Ile Phe Ser
    50                  55                  60

Lys Lys Glu Gly Ser Asp Arg Gln Trp Asn Tyr Ala Cys Met Pro Thr
65                  70                  75                  80

Pro Gln Ser Leu Gly Glu Pro Thr Glu Cys Trp Trp Glu Glu Ile Asn
            85                  90                  95

Arg Ala Gly Met Glu Trp Tyr Gln Thr Cys Ser Asn Asn Gly Leu Val
            100                 105                 110

Ala Gly Phe Gln Ser Arg Tyr Phe Glu Ser Val Leu Asp Arg Glu Trp
        115                 120                 125

Gln Phe Tyr Cys Cys Arg Tyr Ser Lys Arg Cys Pro Tyr Ser Cys Trp
    130                 135                 140

Leu Thr Thr Glu Tyr Pro Gly His Tyr Gly Glu Glu Met Asp Met Ile
145                 150                 155                 160

Ser Tyr Asn Tyr Asp Tyr Tyr Ile Arg Gly Ala Thr Thr Thr Phe Ser
            165                 170                 175

Ala Val Glu Arg Asp Arg Gln Trp Lys Phe Ile Met Cys Arg Met Thr
            180                 185                 190

Glu Tyr Asp Cys Glu Phe Ala Asn Val His His His His His
        195                 200                 205
```

DERMATOPONTIN AS A THERAPEUTIC FOR METABOLIC DISORDERS

CROSS-REFERENCE TO RELATED APPLICATIONS

This patent application is a U.S National Phase application under 35 U.S.C. § 371 of International Applications No. PCT/SG2016/050066, filed on Feb. 11, 2016, entitled DERMATOPONTIN AS A THERAPEUTIC FOR METABOLIC DISORDERS, which claims the benefit of priority of Singapore patent application No. 10201501053Q, filed 11 Feb. 2015, the contents of which were hereby incorporated by reference in their entirety for all purposes.

INCORPORATION BY REFERENCE

This patent application incorporates by reference the material (i.e., Sequence Listing) in the ASCII text file named 9322P074_SeqLsting_111Feb. 2016.txt, created on Feb. 11, 2016, having a file size of 12,719 bytes.

FIELD OF THE INVENTION

The present invention relates generally to the field of biotechnology. In particular, the present invention relates to the field of protein biotechnology.

BACKGROUND OF THE INVENTION

Metabolic diseases such as cardio vascular diseases, diabetes and obesity are a worldwide pandemic with ~382 million people affected by diabetes alone. Currently, there are limited drugs that are effective in combating diabetes. One approach is to hijack biological effects of circulating factors in blood to improve whole body metabolism. Factors such as FGF-21, irisin and adiponectin, which are secreted from the liver, muscles and adipose tissue, respectively, had been previously demonstrated to improve whole body metabolism by modulating various aspects of energy homeostasis.

Therefore, there is a need to identify new therapeutic targets for the treatment of metabolic related diseases.

SUMMARY OF THE INVENTION

In one aspect, the present invention refers to a method of treating a metabolic disease in a subject, wherein the method comprises administration of recombinant dermatopontin to a subject.

In another aspect, the present invention refers to a method of determining or making a prognosis of a subject's susceptibility to metabolic diseases and obesity, the method comprising measuring the level of circulating dermatopontin in a sample obtained from a subject; and comparing the level of circulating dermatopontin obtained with the level of dermatopontin previously determined in a control; and determining the susceptibility of the subject to metabolic disease and obesity based on the difference between the level of circulating dermatopontin and the level of dermatopontin in the control.

In another aspect, the present invention refers to a method of treating a metabolic disease comprising dermatopontin as defined herein.

BRIEF DESCRIPTION OF THE DRAWINGS

The invention will be better understood with reference to the detailed description when considered in conjunction with the non-limiting examples and the accompanying drawings, in which.

DEFINITIONS

Figure 1:
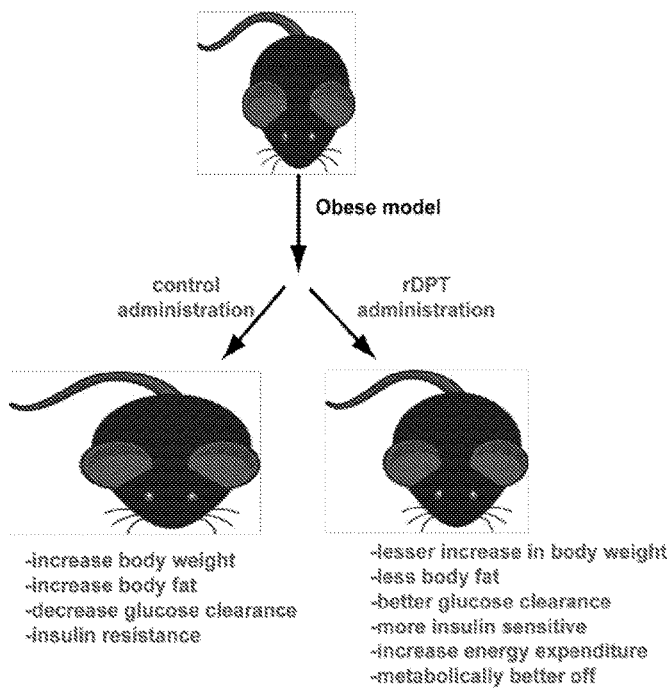
FIG. 1 shows a schematic summarizing the effect of recombinant dermatopontin (rDPT) in an obese mouse model. This summary shows that the administration of recombinant dermatopontin to an obese model mouse results in less body fat, a lesser increase in body weight, better glucose clearance, more insulin sensitivity, increased energy expenditure and improved metabolism compared to an obese model mouse that had been administered a control (saline).

As used herein, the term "recombinant" refers to a nucleic acid sequence or a peptide sequence that is not naturally occurring or was artificially made. Artificial combination is often accomplished by chemical synthesis or, more commonly, by the artificial manipulation of isolated segments of nucleic acids, e.g., by genetic engineering techniques. Similarly, a recombinant protein is a protein that can be encoded by a recombinant nucleic acid molecule. For example, dermatopontin produced by the human body and isolated is not considered to be recombinant.

As defined herein, the terms "peptide", "protein", "polypeptide", and "amino acid sequence" are used interchangeably herein to refer to polymers of amino acid residues of any length. The polymer may be linear or branched, it may comprise modified amino acids or amino acid analogues, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labelling or bioactive component. The term peptide encompasses two or more naturally occurring or synthetic amino acids linked by a covalent bond (e.g., an amide bond). The amino acid residues are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins. The term polypeptide is specifically intended to cover naturally occurring proteins, as well as those that are recombinantly or synthetically produced. Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be performed according to methods known in the art.

As used herein, the term "treatment" refers to any and all uses which remedy a disease state or symptoms, prevent the establishment of disease, or otherwise prevent, hinder, retard, or reverse the progression of disease or other undesirable symptoms in any way whatsoever.

The term "treat" or "treating" as used herein is intended to refer to providing an pharmaceutically effective amount of a peptide or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

As used herein, the term "post-translational modification" refers to modifications that occur on a protein, generally catalysed by enzymes, usually after its translation by ribosomes is complete. Post-translational modification generally refers to the addition of a functional group covalently to a protein, for example as in phosphorylation and neddylation, but also refers to proteolytic processing and folding processes necessary for a protein to mature functionally. Protein post-translational modification increases the functional diversity of the proteome by the covalent addition of functional groups or proteins, proteolytic cleavage of regulatory subunits or degradation of entire proteins. These modifications include, but are not limited to, phosphorylation, glycosylation, sulfation, biotinylation, hydroxylation, acetylation, ubiquitination, nitrosylation, methylation, acetylation, lipidation and proteolysis, and influence almost all aspects of normal cell biology and pathogenesis. Post-translational modification can occur at any step in the "life cycle" of a protein. For example, many proteins are modified shortly after translation is completed to mediate proper protein folding or stability or to direct the nascent protein to distinct cellular compartments (for example, to the nucleus or the cell membrane). Other modifications occur after folding and localization are completed to activate or inactivate catalytic activity or to otherwise influence the biological activity of the protein. Proteins are usually covalently linked to tags that target a protein for degradation. Besides single modifications, proteins are often modified through a combination of post-translational cleavage and the addition of functional groups through a step-wise mechanism of protein maturation or activation. Protein post-translational modifications can also be reversible depending on the nature of the modification. For example, kinases phosphorylate proteins at specific amino acid side chains, which is a common method of catalytic activation or inactivation. Conversely, phosphatases may hydrolyse a phosphate group to remove it from the protein, thereby reversing the biological activity of said protein. The proteolytic cleavage of peptide bonds is a thermodynamically favourable reaction and therefore permanently removes peptide sequences or regulatory domains.

Other protein modifications are also contemplated in the present disclosure. For example, modification of a protein by addition of extraneous peptide sequences, also known as protein tags, to the protein. These peptide sequences are genetically grafted onto the ends of a recombinant protein and can be removed using chemical agents or by enzymatic means, such as proteolysis or intein splicing. Protein tags are attached to proteins for various purposes, for example, the detection, characterisation, purification or any combination of these purposes. For example, an epitope tag can be added to proteins that are otherwise difficult to detect using antibodies. Other uses can also include small or large-scale protein purification based on the physical-chemical properties inferred by such protein tags. Examples of protein tags include, but are not limited to, chitin binding protein (CBP) tag, maltose binding protein (MBP) tag, epitope tag, glutathione-S-transferase (GST) tag, polyarginine tag, polyhistidine tag, hexa histidine tag, poly-FLAG tag, FLAG tag, c-myc tag, human influenza hemagglutinin (HA) tag, S-fragment of RNA (S-) tag, natural histidine affinity (HAT) tag, streptavidin (SBP) tag, calmodulin binding protein tag, cellulose binding protein tag, fluorescent protein tag, green fluorescent protein (GFP) tag. In one example, the protein as described herein comprises a histidine tag. In another example, the protein tag is a hexa histidine tag. These protein tags can be attached to either the N- or the C-terminal, or both the N- and C-termini of the protein. In one example, the tag is attached to the N-terminus of the protein. In another example, a tag is attached to the C-terminus of the protein. In yet another example, the protein as described herein comprises a hexa histidine tag at its C-terminus.

In the context of this disclosure the term "administering" and variations of that term including "administer" and "administration", includes contacting, applying, delivering or providing a compound or composition to an organism, or a surface by any appropriate means.

As used herein, the term "bioavailability" refers to the degree and rate at which a substance, for example a drug, peptide or hormone, is made available at the site of physiological activity. In the art of pharmacology, the term "bioavailability" is understood to refer to the fraction of an administered dose of unchanged drug, compound or medicament, that reaches the systemic circulation, one of the principal pharmacokinetic properties of drugs. By definition, when a medication is administered intravenously, its bioavailability is 100%. However, when a compound is administered via other routes (e.g. orally or intramuscularly), its bioavailability generally decreases due to factors, such as incomplete absorption and first-pass metabolism. These factors may vary from patient to patient due to, for example, differences in individual metabolism.

As used herein, the term "uptake" refers to the process by which something (e.g. a compound, drug or medicament) is taken in by an organism, for example a mammalian body or a plant.

As used herein, the term "adipokine" refers to specific type of cytokines (cell signalling proteins) secreted by adipose tissue. In turn, the term "cytokines" refers to cell signalling proteins, which are a broad and loose category of small proteins, roughly about 5 to 20 kDa in size. These cytokines are released by various types of cells and have an effect on the behaviour of other cells. These cells may be neighbouring cells but may also be cells greater distances away. Cytokines can also be involved in autocrine signalling. Cytokines may include, but are not limited to, chemokines, interferons, interleukins, lymphokines and tumour necrosis factors, but generally do not include hormones or growth factors, despite some overlap in the terminology used in the art. Cytokines are produced by a broad range of cells, including, but not limited to, immune cells like macrophages, B lymphocytes, T lymphocytes and mast cells, as well as endothelial cells, fibroblasts, and various stromal cells. It is possible for a given cytokine may be produced by more than one type of cell.

As used herein, the term "high expression" denotes a level of expression of, for example, dermatopontin in subcutaneous fat depots, which is above a level found in adipose cells isolated or cultivated from other parts of a subject. For example, the amount of dermatopontin that may be found in white adipose tissue may be higher compared to the amount of dermatopontin that may be found in brown adipose tissue from the same subject.

As used herein, the term "homologue" refers to a degree of similarity, for example, in position or structure. In terms of the present disclosure, homologous peptides are peptides that may indicate a common origin, for example between species. Usually, homologous proteins share common structural features and functions, however this does not necessarily imply that the homologous proteins have an identical or similar peptide sequence. A homologous peptide can have an identical sequence with the target, comparison protein. It is also possible that a homologous peptide can have a sequence that differs to varying degrees from that of the target, comparison protein. The determining factor of the homology is thus the functionality of the homologue.

As used herein, "substantially pure" or "substantially free of contaminants" means an object species is the predominant species present (e.g., on a molar basis it is more abundant than any other individual species in the composition), and preferably a substantially purified fraction is a composition wherein the object species comprises at least about 50% (on a molar basis) of all macromolecular species present. Generally, a substantially pure composition will comprise more than about 80% of all macromolecular species present in the composition. In one example, the substantially pure composition comprises more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

As used herein, the term "conserved" refers to any sequence of bases (or amino acids) in comparable segments of different nucleotides (or proteins) that tend to show similarity greater than that due to chance alone. For example, if one position is occupied by the same base in all comparable DNA sequences, then that position is said to be completely conserved. If the same base occurs at a given position in, for example, 75% of samples examined, it would be described as partially conserved. By extension, the conservation of other positions in a sequence is assessed in the same way, usually by computer analysis. The degree in which sequences are conserved can indicate the extent of structural and functional similarities between different genes or between different proteins and provides clues to their possible evolutionary relations. The term "conserved" can be appended with the term "highly", indicating that the conserved sequences in question contain minimal variations between them. Sequences that do not show any similarities between them would not be considered to be "conserved" sequences.

DETAILED DESCRIPTION OF THE PRESENT INVENTION

Cardio vascular diseases, diabetes, obesity and other metabolic diseases are a worldwide pandemic, with roughly 382 million people being affected by diabetes alone. As an example, there are currently limited drugs that are effective in combating diabetes. In the search for new treatments for metabolic diseases, one approach has been to hijack biological effects of circulating factors in blood in order to improve whole body metabolism.

Dermatopontin is also known to be an adipocyte marker, which is highly expressed in depots of white adipose cells, but not in depots of brown adipose cells. However, the biological role of dermatopontin in adipose tissue has not been described. The present invention elucidates the role of dermatopontin in adipose tissue and finds that dermatopontin plays a role in controlling the whole body metabolism. Dermatopontin is an adipokine, which is highly expressed in the subcutaneous fat depot. In mice, administration of dermatopontin is shown to increase energy expenditure of the subject without affecting other parameters, such as food intake and movement, whereas, for example as a comparison, whole body dermatopontin knockout mice showed the opposite. That is to say, in a dermatopontin knockout mouse, in which the gene for expressing dermatopontin had been irreversibly removed, these mice show that the lack of dermatopontin resulted in lower energy expenditure compare to mice that had been treated with (recombinant) dermatopontin. Therefore, identifying the molecular targets of dermatopontin and the physiological regulator of the expression of dermatopontin impacts and shows how dermatopontin and derivatives thereof are used as therapeutic compounds or therapeutic biologicals for metabolic related diseases.

Thus, in one example, the present disclosure describes use of dermatopontin, or derivatives thereof, in the manufacture of a medicament for the treatment of a metabolic disease. In another example, a method of treating a metabolic disease is a subject is disclosed. In yet another example, the dermatopontin is recombinant dermatopontin. In a further example, the metabolic disease can be, but is not limited to, weight gain, diet-induced weight gain, reduction in fat mass, weight gain-associated obesity, obesity, morbid obesity, metabolic syndrome, glucose homeostasis, insulin resistance, type I diabetes, type II diabetes and cardiovascular disease.

Dermatopontin (DPT), a 22 kDa extracellular matrix protein first identified in bovine skin, is known in the art to be involved in cell adhesion and proliferation. Thus, in one example, the recombinant dermatopontin is of mammalian origin. In another example, the recombinant dermatopontin is of human, bovine, porcine or murine origin. In yet another example, the recombinant dermatopontin is of human origin. In one example, the recombinant dermatopontin comprises a sequence which can be, but is not limited to SEQ ID NO: 1, SEQ ID NO: 2, SEQ ID NO: 3, SEQ ID NO: 4, or SEQ ID NO: 12. In yet another example, the recombinant dermatopontin comprises SEQ ID NO: 1.

Dermatopontin is known in the art to be a protein that is well conserved over many mammals and some invertebrates. Therefore, the present disclosure also describes the use of dermatopontin from other species other than those described herein. This, in one example, the use is as described herein, wherein the recombinant dermatopontin is a homologue of any one of SEQ ID NO: 1, SEQ ID NO: 2, SEQ ID NO: 3, SEQ ID NO: 4 or SEQ ID NO: 12 with a sequence identity of between 60% to 99%, between 80% and 95%, at least 60%, at least 65%, at least 70%, at least 75%, at least 80%, at least 85%, at least 87%, at least 90%, at least 91%, at least 92%, at least 93%, at least 94%, at least 95%, at least 96%, at least 97%, at least 98%, at least 99%, about 67%, about 77%, about 82%, about 88%, about 93% or about 98%.

The present disclosure also describes post-translationally modified versions of the recombinant dermatopontin protein. Post-translational modifications can occur on the amino acid side chains or at the protein's C- or N-termini. They can extend the chemical repertoire of the twenty standard amino acids by introducing new functional groups such as phosphate, acetate, amide groups, or methyl groups. Phosphorylation is known in the art as a very common mechanism for regulating the activity of enzymes and is the most common post-translational modification. Many eukaryotic proteins also have carbohydrate molecules attached to them in a process called glycosylation, which can promote protein folding and improve stability, as well as serving various regulatory functions. Attachment of lipid molecules, known as lipidation, often targets a protein or part of a protein to the cell membrane. Thus, in one example, the recombinant dermatopontin is modified at its C-terminus or N-terminus. In another example, the recombinant dermatopontin is post-translationally modified. In yet another example, the post-translational modification is selected from, but not limited to, glycosylation, sulfation, phosphorylation, ubiquitination, methylation, lipidation, biotinylation, hydroxylation and acetylation. In another example, the peptide is modified to include one or more ligands selected from, but not limited to, hydroxyl, phosphate, amine, amide, sulphate, sulphide, a biotin moiety, a carbohydrate moiety, a fatty acid-derived acid group, a fluorescent moiety, a chromophore moiety, a radioisotope, a polyethylene-glycol (PEG) linker, an affinity label, a targeting moiety, an antibody, a cell penetrating peptide or a combination of the aforementioned ligands Also described herein is recombinant dermatopontin that has been modified at its C- or N-terminus by the addition of an additional secretory signals or signalling peptides. One example known in the art is the addition of a nuclear localisation sequence (NLS) which directs the nascent protein for import from the cytoplasm into to the nucleus of the cell. There are many different versions of nuclear localisation sequences and their length and composition is dependent on the call type from which they have been isolated. For example, the nuclear localisation sequence of nucleoplasmin is "AVKRPAATKKAGQAKKKKLD" (SEQ ID NO: 9), whereas the nuclear localisation sequence of c-myc is "PAAKRVKLD" (SEQ ID NO: 10). Another example of a signalling peptide known in the art is a nuclear export signal (NES), which is tagged onto a nascent protein that is to be exported from the cell nucleus into the cytoplasm. These nuclear export signals (NES) are usually a short amino acid sequence of 4 hydrophobic residues. Therefore, in one example, the recombinant dermatopontin consists of a highly conserved secretory signal at its N-terminus. In another example, the secretory signal comprises a sequence selected from the group consisting of SEQ ID NO: 6, SEQ ID NO: 7 or SEQ ID NO: 8.

Any of the modifications to dermatopontin may or may not have an effect on the bioavailability of dermatopontin, which is the amount of dermatopontin that is ultimately available at the site of required activity after being administered to the subject. Also, any modifications to dermatopontin may or may not have an effect of the uptake of dermatopontin in the target cells of the subject. Also the metabolism of the body of a subject given dermatopontin will determine how much dermatopontin is made available at the site of action, thereby determining the individual pharmacokinetic of, for example, a recombinant or modified dermatopontin. Factors known to influence the bioavailability of peptides and proteins and are specific depending on the route of intended administration. For example, the enzymatic stability of the peptide, the aqueous solubility and the lipid layer penetration in order to the peptide to cross, e.g. the intestinal and subsequently the basal membrane for entry into the bloodstream are some of the factors which, among others, need to be address when formulating a protein composition for oral delivery. Thus, in one example, the recombinant dermatopontin is modified to influence uptake or bioavailability of said dermatopontin.

The nucleic acid molecule disclosed herein may comprise a nucleotide sequence encoding the peptide serving as template for peptides disclosed herein, which can be operably linked to a regulatory sequence to allow expression of the nucleic acid molecule. A nucleic acid molecule, such as DNA, is regarded to be 'capable of expressing a nucleic acid molecule or a coding nucleotide sequence' or capable 'to allow expression of a nucleotide sequence' if it contains regulatory nucleotide sequences which contain transcriptional and translational information and such sequences are "operably linked" to nucleotide sequences which encode the polypeptide. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced polypeptide to a specific compartment of a host cell, which is used for producing a peptide described above.

The nucleic acid molecule comprising the nucleotide sequence encoding the peptide as disclosed herein can be comprised in a vector, for example an expression vector. Such a vector can comprise, besides the above-mentioned regulatory sequences and a nucleic acid sequence which codes for a peptide as described above, a sequence coding for restriction cleavage site which adjoins the nucleic acid sequence coding for the peptide in 5' and/or 3' direction. This vector can also allow the introduction of another nucleic acid sequence coding for a protein to be expressed or a protein part. The expression vector preferably also contains replication sites and control sequences derived from a species compatible with the host that is used for expression. The expression vector can be based on plasmids well known to person skilled in the art such as pBR322, puC16, pBluescript and the like.

The vector containing the nucleic acid molecule can be transformed into host cells capable of expressing the genes. The transformation can be carried out in accordance with standard techniques. Thus, the disclosure is also directed to a (recombinant) host cell containing a nucleic acid molecule as defined above. In this context, the transformed host cells can be cultured under conditions suitable for expression of the nucleotide sequence encoding the peptide as described above. Host cells can be established, adapted and completely cultivated under serum free conditions, and optionally in media which are free of any protein/peptide of animal origin. Commercially available media such as RPMI-1640 (Roswell Park Memorial Institute 1640), Dulbecco's Modified Eagle's Medium (DMEM), Minimal Essential Medium (MEM), CHO-S-SFMII, serum free-CHO Medium, and protein-free CHO (Chinese hamster ovary cells) Medium are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES (4-(2-hydroxyethyl)-1-piperazineethanesulfonic acid)), nucleosides (such as adenosine, thymidine), glutamine, glucose or other equivalent energy sources, antibiotics, trace elements. Any other necessary supplements may also be included at appropriate concentrations that are known to those skilled in the art. Therefore, in one example, the present disclosure describes a nucleic acid sequence capable of expressing the recombinant dermatopontin as described herein. In another example, the nucleic acid sequence of the recombinant dermatopontin consists of SEQ ID NO: 5.

A peptide as described herein, or pharmaceutical composition or medicament thereof, can be administered in a number of ways depending upon whether local or systemic administration is desired and upon the area to be treated. For example, the peptide or the respective pharmaceutical composition thereof can be administered to the patient orally, or rectally, or transmucosally, or intestinally, or intramuscularly, or subcutaneously, or intramedullary, or intrathecally, or direct intraventricularly, or intravenously, or intravitreally, or intraperitoneally, or intranasally, or intraocularally. Thus, in one example, the present disclosure describes the use of the protein as described herein as a medicament, wherein the medicament is to be administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravenously, intravesicularlly, intravitreally, liposomally, locally, mucosally, orally, enterally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion or any combination thereof.

The peptides themselves may be present in the compositions in any of a wide variety of forms. For example, two, three, four or more peptides may be merely mixed together or may be more closely associated through complexation, crystallization, or ionic or covalent bonding. The peptides can also encompass any pharmaceutically acceptable salts, esters, or salts of such esters, or any other compound, which, upon administration to an animal, including a human, is capable of providing the biologically active metabolite or residue thereof. Accordingly, also described herein is drawn to prodrugs and pharmaceutically acceptable salts of such pro-drugs, and other bioequivalents. Therefore, in one example, the protein as disclosed here, for example as a medicament, is to be administered with at least one or two or more therapeutic agents.

The present disclosure also describes combination therapies and compositions, that is to say that the peptide, as described herein, may be administered simultaneously, sequentially or separately, or combinations thereof, from a further therapeutic compound or therapeutic agent. Thus, in one example, the administration is simultaneous, that is to say that both the recombinant dermatopontin and the further therapeutic agent are to be administered at the same time. In another example, the recombinant dermatopontin and the further therapeutic agent are to be administered separately. In yet another example, the recombinant dermatopontin and the further therapeutic agent are to be administered sequentially, that is to say that for example recombinant dermatopontin can be administered first, followed by administration of the further therapeutic compound. Alternatively, in another example, the further therapeutic agent can be administered first, followed by the administration of the recombinant dermatopontin. In yet another example, a first therapeutic agent is to be administered, after which the recombinant dermatopontin is administered, followed by the administration of a second therapeutic agent. In a further example, one therapeutic agent is to be administered, followed by the subsequent administration of the recombinant dermatopontin simultaneously with a second therapeutic agent. A therapeutic agent can be, but is not limited to, small molecules, biologics, chemotherapies, supplements or biotechnology-derived products; orlistat, locaserin, sibutramine, rimonabant, metformin, exenatide, pramlintide, phentermine, topiramate; insulin, acetylsalicylic acid, acarbose, miglitol, alogliptin, linagliptin, pioglitazone, saxagliptin, sitagliptin, simivastin, albiglutide, dulaglutide, liraglutide, nateglinide, repaglinide, dapagliflozin, canagliflozin, empagliflozin, glimepiride, rosiglitazone, gliclazide, glipizide, glyburide, chlorpropamide, tolazamide, tolbutamide and combinations thereof.

The peptide, the isolated nucleic acid molecule or the vector as described herein and above can be formulated into compositions, for example pharmaceutical compositions, suitable for administration. Where applicable, a peptide may be administered with a pharmaceutically acceptable carrier. A "carrier" can include any pharmaceutically acceptable carrier as long as the carrier can is compatible with other ingredients of the formulation and not injurious to the patient. Accordingly, pharmaceutical compositions for use may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Thus, in one example, the present disclosure described a pharmaceutical composition comprising, but not limited to, a peptide as described herein, an isolated nucleic acid molecule as described herein or a vector as described herein. In another example, the present disclosure describes an isolated nucleic acid molecule encoding a peptide as described herein. In yet another example, the present disclosure describes a vector comprising an isolated nucleic acid molecule as described herein. In one example, the pharmaceutical composition comprises a peptide as described herein. In yet another example, the pharmaceutical composition further comprises one or more pharmaceutically acceptable excipients, vehicles or carriers. Therefore, in one example, the peptide as disclosed herein may further comprise a compound selected from, but not limited to, a pharmaceutically acceptable carrier, a liposomal carrier, an excipient, an adjuvant or combinations thereof.

The composition, shape, and type of dosage forms of the peptide as disclosed herein will typically vary depending on the intended use. For example, a dosage form used in the acute treatment of a disease or a related disease may contain larger amounts of one or more of the active compound it comprises than a dosage form used in the chronic treatment of the same disease. Similarly, a parenteral dosage form may contain smaller amounts of one or more of the active compound it comprises than an oral dosage form used to treat the same disease or disorder. These and other ways in which specific dosage forms encompassed by this invention will vary from one another will be readily apparent to those skilled in the art. Examples of dosage forms include, but are not limited to: tablets; caplets; capsules, such as soft elastic gelatine capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient. Thus, in one example, the peptide as disclosed herein is provided in a form selected from, but not limited to, tablets, caplets, capsules, hard capsules, soft capsules, soft elastic gelatine capsules, hard gelatine capsules, cachets, troches, lozenges, dispersions, suppositories, ointments, cataplasms, poultices, pastes, powders, dressings, creams, plasters, solutions, patches, aerosols, nasal sprays, inhalers, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof. is to be administered at an amount of between 0.1 mg/kg and 10 mg/kg, between 0.1 mg/kg and 5 mg/kg, between 1 mg/kg to 2.5 mg/kg, between 2.5 mg/kg to 5 mg/kg, between 5 mg/kg and 10 mg/kg, between 5 mg/kg and 7.5 mg/kg, between 7.5 mg/kg and 10 mg/kg, at least 1 mg/kg, at least 1.5 mg/kg, at least 1.8 mg/kg, at least 2 mg/kg, at least 2.5 mg/kg, at least 2.8 mg/kg, at least 3 mg/kg, at least 3.2 mg/kg, at least 3.5 mg/kg, at least 4 mg/kg, at least 4.5 mg/kg, at least 5 mg/kg, at least 5.5 mg/kg, at least 6 mg/kg, at least 6.5 mg/kg, at least 7 mg/kg, at least 7.5 mg/kg, at least 8 mg/kg, at least 8.5 mg/kg, at least 9 mg/kg, at least 9.5 mg/kg or at least 10 mg/kg. In one example, the amounts to be administered, as described herein, are to be understood as the dosage regime per day. In another example, the medicament is to be administered to a subject daily, weekly, twice a week (bi-weekly), three times a week, every two weeks, monthly (that is to say once a month) or any combinations thereof. For example, the medicament may be administered daily for the first week and twice weekly for 4 subsequent weeks. Or, the medicament can be administered to a subject bi-weekly for the first 2 weeks of treatment and then monthly for further 3 months.

Like the amounts and types of excipients, the amounts and specific types of active compound in a dosage form may differ depending on factors such as, but not limited to, the route by which it is to be administered to patients. However, typical dosage forms of the present disclosure comprise recombinant dermatopontin, or a pharmaceutically acceptable salt, hydrate, or stereoisomers thereof and can further comprise between 0.1 mg to 1500 mg per administration unit to provide doses between 0.01 mg/kg to 200 mg/kg per day. In one example, the daily dose of the protein as described herein is between 0.1 mg to 5 mg, between 5 mg to 50 mg, between 50 mg to 100 mg, between 100 mg to 500 mg, between 500 mg to 1000 mg, between 1000 mg to 1500 mg, about 20 mg, about 30 mg, about 35 mg, about 45 mg, about 55 mg, about 70 mg, about 80 mg, about 85 mg, about 120 mg, about 250 mg, about 320 mg, about 450 mg, about 520 mg, about 680 mg, about 750 mg, about 800 mg, about 990 mg, about 1200 mg, at least 500 mg, at least 600 mg, at least 800 mg, at least 1300 mg or at least 1400 mg.

The medicament as described herein may be administered to a subject in need thereof. In one example, the subject to be treated is mammalian. In another example, the subject is human.

The protein as described herein is also used in a method for determining or making a prognosis of a subject's susceptibility to metabolic diseases and obesity. The modes of analysing the levels of the target protein in a subject may be performed using methods known in the art. Therefore, in one example, disclosed herein is a method of determining or making a prognosis of a subject's susceptibility to metabolic diseases and obesity, the method comprising measuring the level of circulating dermatopontin in a sample obtained from a subject; comparing the level of circulating dermatopontin obtained previously with the level of dermatopontin previously determined in a control; and determining the susceptibility of the subject to metabolic disease and obesity based on the difference between the level of circulating dermatopontin and the level of dermatopontin in the control. In another example, the method of determining or making a prognosis of a subject's susceptibility to metabolic diseases and obesity can further comprise administration of, for example recombinant dermatopontin, to a subject deemed to be in need of treatment based on the method as described herein.

The comparison of concentrations or levels of a target protein or analyte in a subject are determined based on the comparison of the level of target analyte determined in the subject and the level of target analyte determined in a control group or control individual. In the present disclosure, the control is a subject that is disease-free. That is, the control is a subject that is free of the disease for which the test is undertaken. Usually, the term disease-free implies that the subject is healthy.

In another example, the present disclosure describes a method of treating a metabolic disease comprising administered to a subject in need thereof, dermatopontin, recombinant dermatopontin or derivatives thereof, as defined herein. In yet another example, the metabolic disease to be treated is selected from, but not limited to, weight gain, diet-induced weight gain, reduction in fat mass, obesity, morbid obesity, metabolic syndrome, glucose homeostasis, insulin resistance, type I diabetes, type II diabetes and cardiovascular disease.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Figure 2:
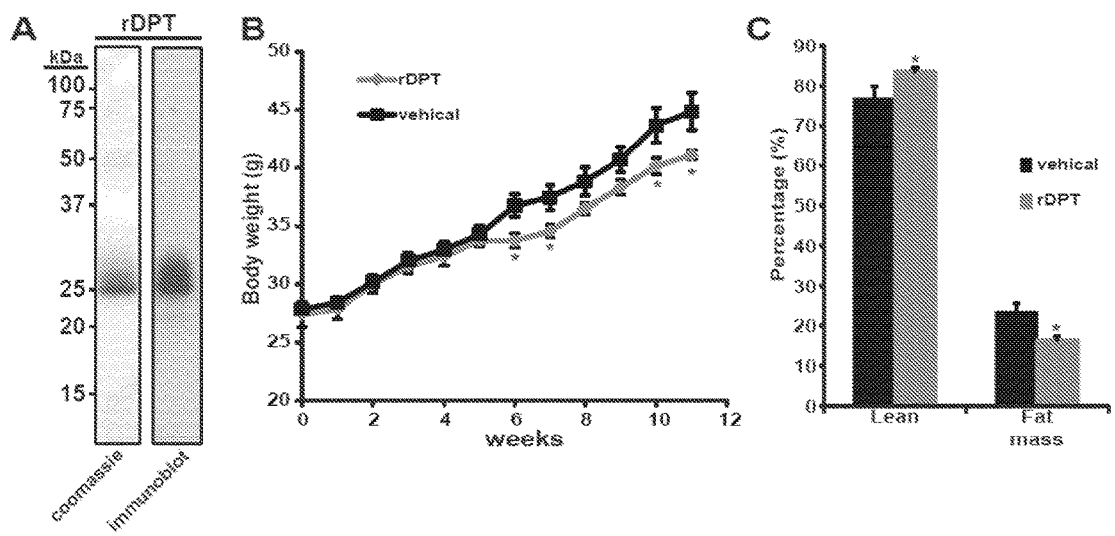
FIG. 2 shows results of the administration of recombinant dermatopontin (rDPT) in a mouse model. Taken together, this data shows that the injection of recombinant dermatopontin increases whole body energy expenditure and improve whole body metabolism, compared to mice that had been administered a vehicle (saline). A) shows a coomassie blue staining (left column) and a western blot (right column) of recombinant dermatopontin produced in a yeast system engineered to express the human DPT gene. B) is a line graph showing the change in body weight of mice that had been treated with a vehicle (negative control) or recombinant dermatopontin (rDPT), thereby showing that rDPT-treated mice showed a lower increase in body weight over time. C) is a column chart showing the distribution of total lean mass and total fat mass (in percentage) in vehicle or recombinant dermatopontin (rDPT) injected mice. This shows that the mice treated with rDPT are shown to have a higher percentage of lean mass compared to vehicle-treated mice. D) is a line graph showing the results of a glucose tolerance test (GTT) performed on vehicle or recombinant dermatopontin (rDPT) injected mice at week 4 post-treatment, showing that rDPT-treated mice had an overall lower blood glucose level after ingesting glucose compared to vehicle-treated mice. E) shows a column chart representing the Area under the curve (AUC) for the glucose tolerance test (GTT) data previously shown in D), whereby the AUC determined for rDPT-treated mice is less than the AUC determined for vehicle-treated mice. F) is a line graph showing the results of an insulin tolerance test (ITT) performed on a group of mice treated with a vehicle and a group of mice treated with recombinant dermatopontin (rDPT) at week 9 post-treatment. This data shows that the mice treated with rDPT have a lower blood glucose level than mice treated with a vehicle. G) shows a column chart representing the Area above the curve (AAC) of the insulin tolerance test shown previously in F). The Area above the curve (AAC) is a mathematical concept similar to that of "Area under the curve" (that is defined integration), which is commonly used to determine the total concentration of an observed variable over a period of time. To obtain the Area above the curve (AAC) for the present example, the Area under the curve (AUC) value is calculated first. Then, to calculate the AUC, the sum of the trapezoidal area is calculated for the time points 15, 30, 45, 60 and 90 min. To calculate the AAC, the AUC value is then subtracted from the total area of the graph (for example, 0 to 12 on the x-axis multiply by 0 to 90 of the y-axis). In this example, the AAC is used to determine the concentration of glucose in the blood stream after insulin injection. H) shows a line graph (including the individual standard deviations calculated for each data point) depicting the energy expenditure of a group of mice treatment with either the vehicle (saline) or recombinant dermatopontin (rDPT) at week 11 post-treatment. This graph shows that rDPT-treated mice exhibit and increased energy expenditure during both light and dark hours compared to saline-treated mice. I) is a column chart showing the quantified, average energy expenditure of the energy expenditure previously shown in H), further showing that the average energy expenditure for rDPT-treated mice is overall higher compared to the average energy expenditure of vehicle-treated mice. The following criteria apply for all of FIG. 2: n=4 for vehicle injected group and n=5 for rDPT injected group. *p<0.05, p<0.01, *p<0.005.
Figure 2:
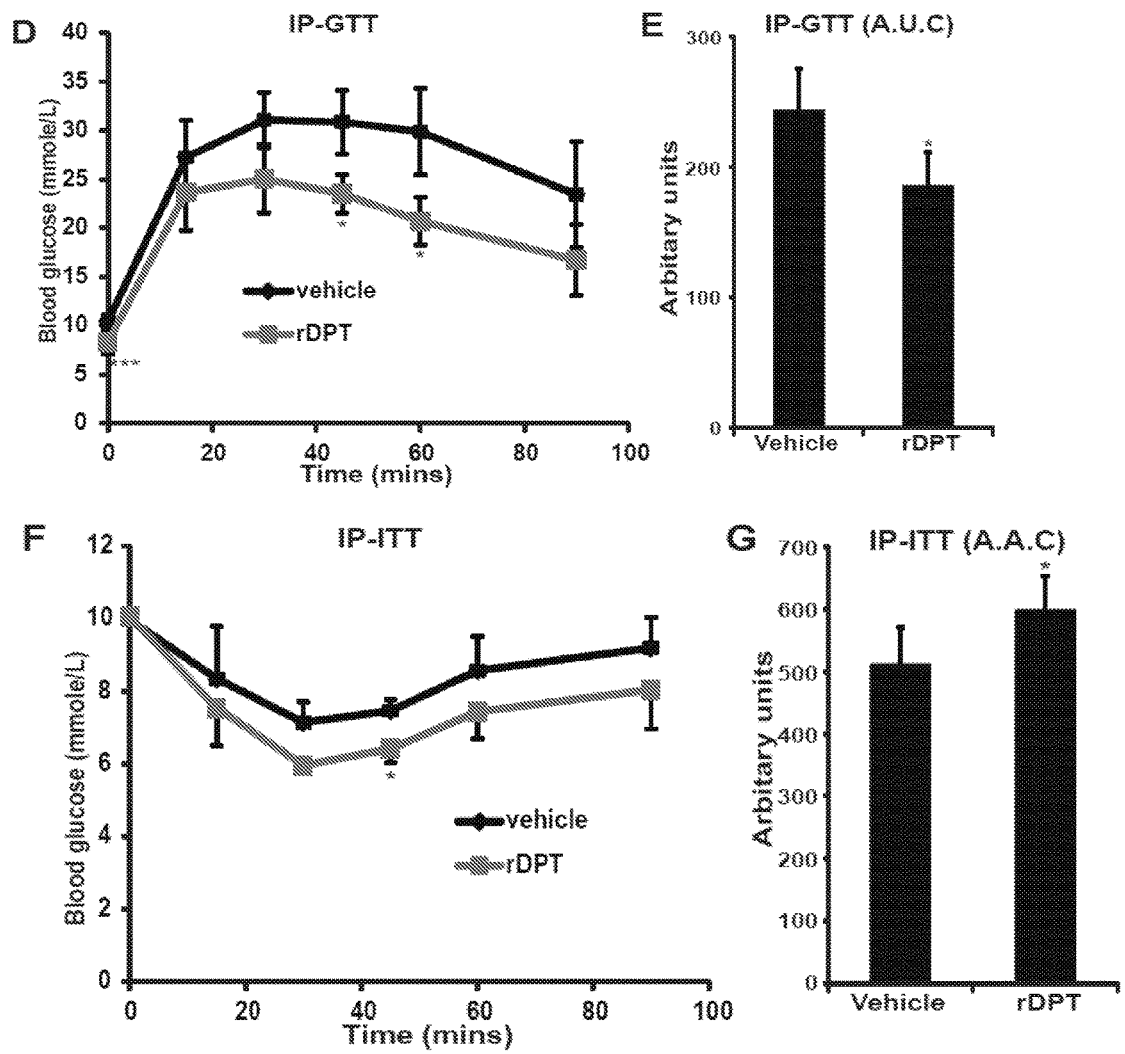
Figure 2:
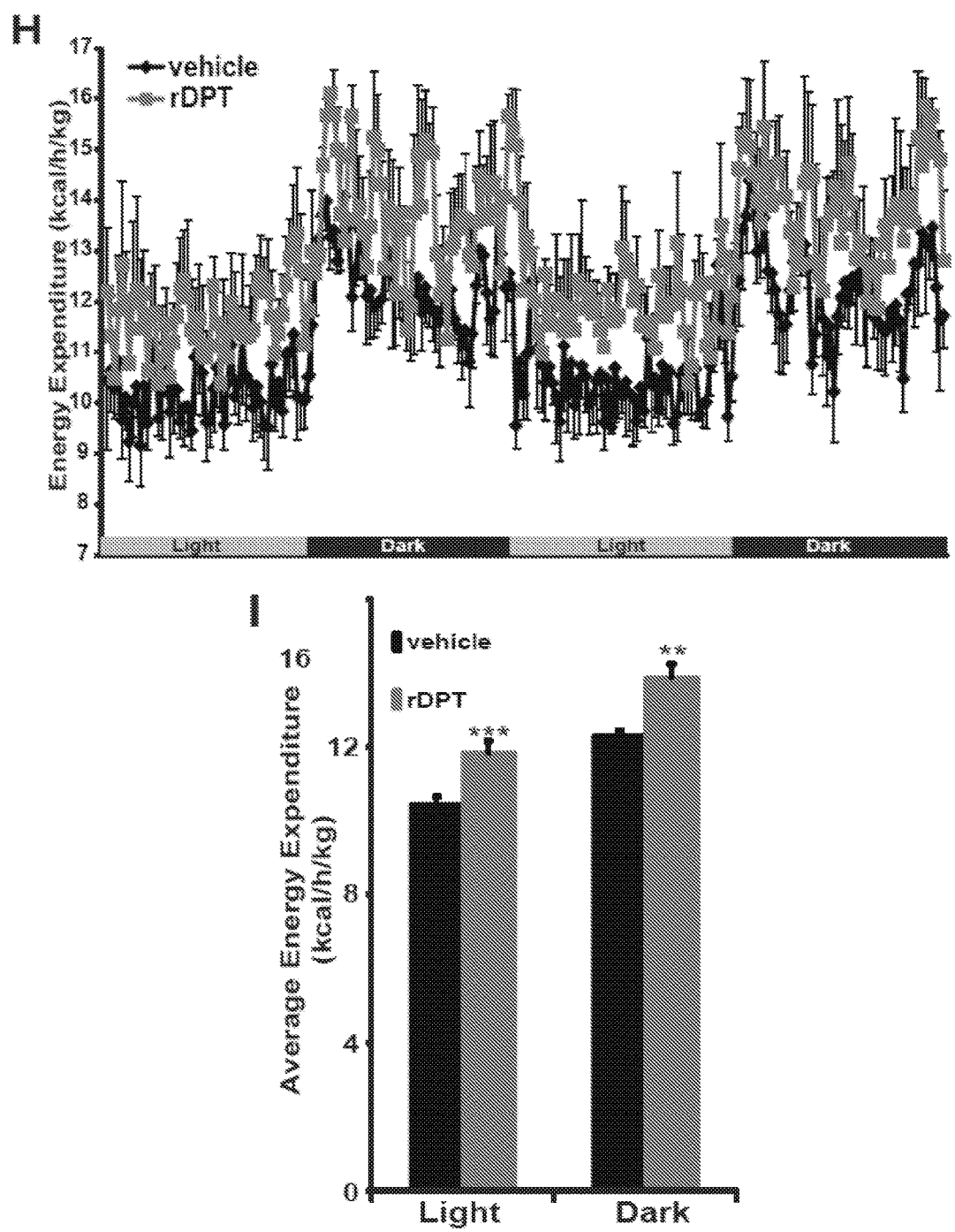

Recombinant Dermatopontin (rDPT) Reduces Weight Gain Induced by High Fat Diet Feeding To determine the effect of recombinant dermatopontin (rDPT) in mice, recombinant dermatopontin was first produced and its purity determined. The produced protein was determined to be of similar size to that of natural dermatopontin, which is a ~22 kDa protein. Recombinant dermatopontin was detected via Western blot or immunoblotting using antibodies specific against dermatopontin (FIG. 2A). Coomassie blue staining showed that the produced recombinant dermatopontin is substantially free of any contaminating proteins (FIG. 2A).

To determine whether recombinant dermatopontin had any effect on metabolism, mice were injected mice with recombinant dermatopontin at 2 mg/kg body weight of the mouse, three times a week for the duration of one week. Control mice were injected with the same volume of vehicle (namely saline solution). All mice were then fed a standard CHOW diet for 2 weeks after the injections had been administered. Prior to receiving the injections, all mice were fed were fed a high fat diet to accelerate weight gain and induce insulin resistance. The group of mice which had been injected with recombinant dermatopontin showed lesser weight gain when compared to vehicle control group (FIG. 2B). Without being bound by theory, it is understood that this is due to a reduction in fat mass in the group treated with recombinant dermatopontin (FIG. 2C).

Recombinant Dermatopontin (rDPT) Improves Glucose Clearance and Insulin Sensitivity To test if recombinant dermatopontin has any effect on subject metabolism, both the recombinant dermatopontin treated group and the vehicle-treated group were challenged with a bolus of glucose via intra-peritoneal injection (IP-GTT; FIGS. 2D and E). The data shows that the recombinant dermatopontin-injected group displayed an improved glucose clearance compared to control mice (FIGS. 2D and E).

Without being bound by theory, the improvement in glucose disposal based on the results of the glucose tolerance test (GTT) are due to either an improvement of insulin secretion by the pancreas or increased insulin sensitivity of the peripheral tissues (e.g. insulin-responsive muscle, liver and adipose). An insulin tolerance test (ITT) was performed to determine whether it is the former or latter that mediates the improvement in glucose clearance. The recombinant dermatopontin-injected group showed an improved glucose disposal during the insulin tolerance test (ITT; FIGS. 2F and G), suggesting that recombinant dermatopontin leads to improve peripheral insulin sensitivity.

Figure 8:
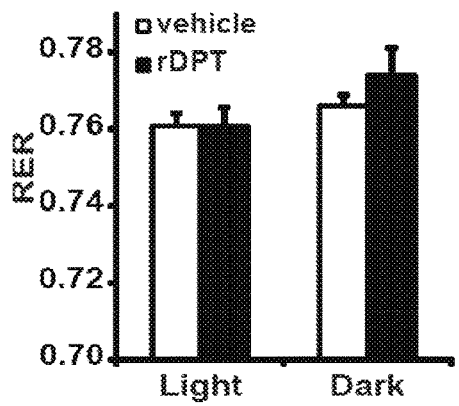
FIG. 8 shows data showing the effect of recombinant dermatopontin (rDPT) injection into mice on high fat diet. (A) shows histograms depicting various measurements taken from mice, for example the respiratory exchange ratio (RER), (B) X-axis movement, (C) Y-axis movement, (D) Food intake and (E) water intake of mice injected with vehicle or recombinant dermatopontin (rDPT).
Figure 8:
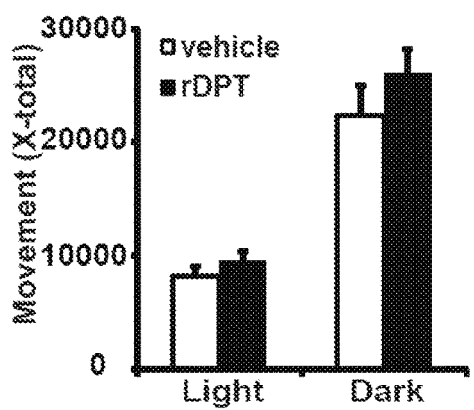
Figure 8:
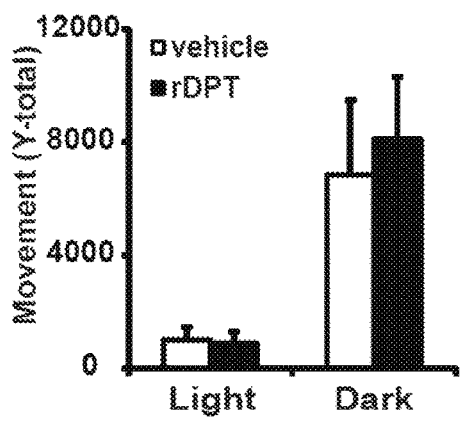
Figure 8:
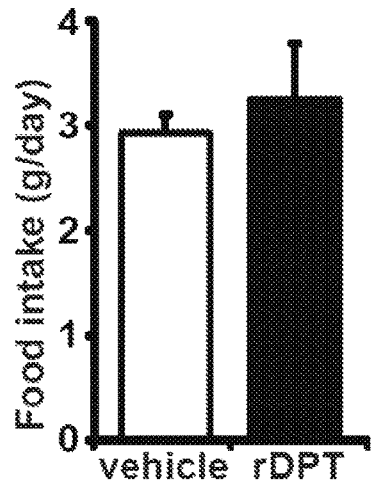
Figure 8:
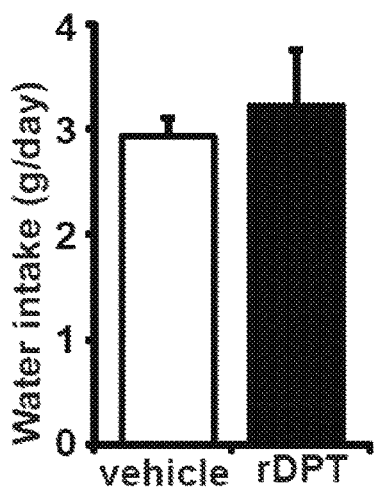

Recombinant Dermatopontin (rDPT) Increases Energy Expenditure without Affecting Food Intake and Movement The effect of recombinant dermatopontin on whole body metabolism was analysed by using a Comprehensive Laboratory Animal Monitoring System (CLAMS), with which various metabolic parameters, including energy expenditure, movement of animals, food intake and the like can be determined. The data shows that mice injected with recombinant dermatopontin have an increased energy expenditure during periods where there is usually less movement (light cycle) and also during period where the mice are usually more active (dark cycle; FIGS. 2H and I). No change in food intake, water intake or movement was detected (FIG. 8). These results show that recombinant dermatopontin exert its effects, at least in part, through an increase in energy expenditure.

Thus, recombinant dermatopontin, for example isolated from human, can be used as a therapeutic against weight gain, reduces gain in fat mass, improves glucose clearance and peripheral insulin sensitivity and increases energy expenditure. We proposed that rDPT can be used as therapeutics to combat weight gain in subjects, thus reducing the risk of obesity and diabetes. Given that diabetes and/or obesity are closely linked to other metabolic disorders, such as cardiovascular diseases, recombinant dermatopontin can be used as a therapeutic for these and other metabolic disorders or metabolism related diseases.

Dermatopontin is Highly Expressed in Adipocyte and is Found in Circulation

Figure 3:
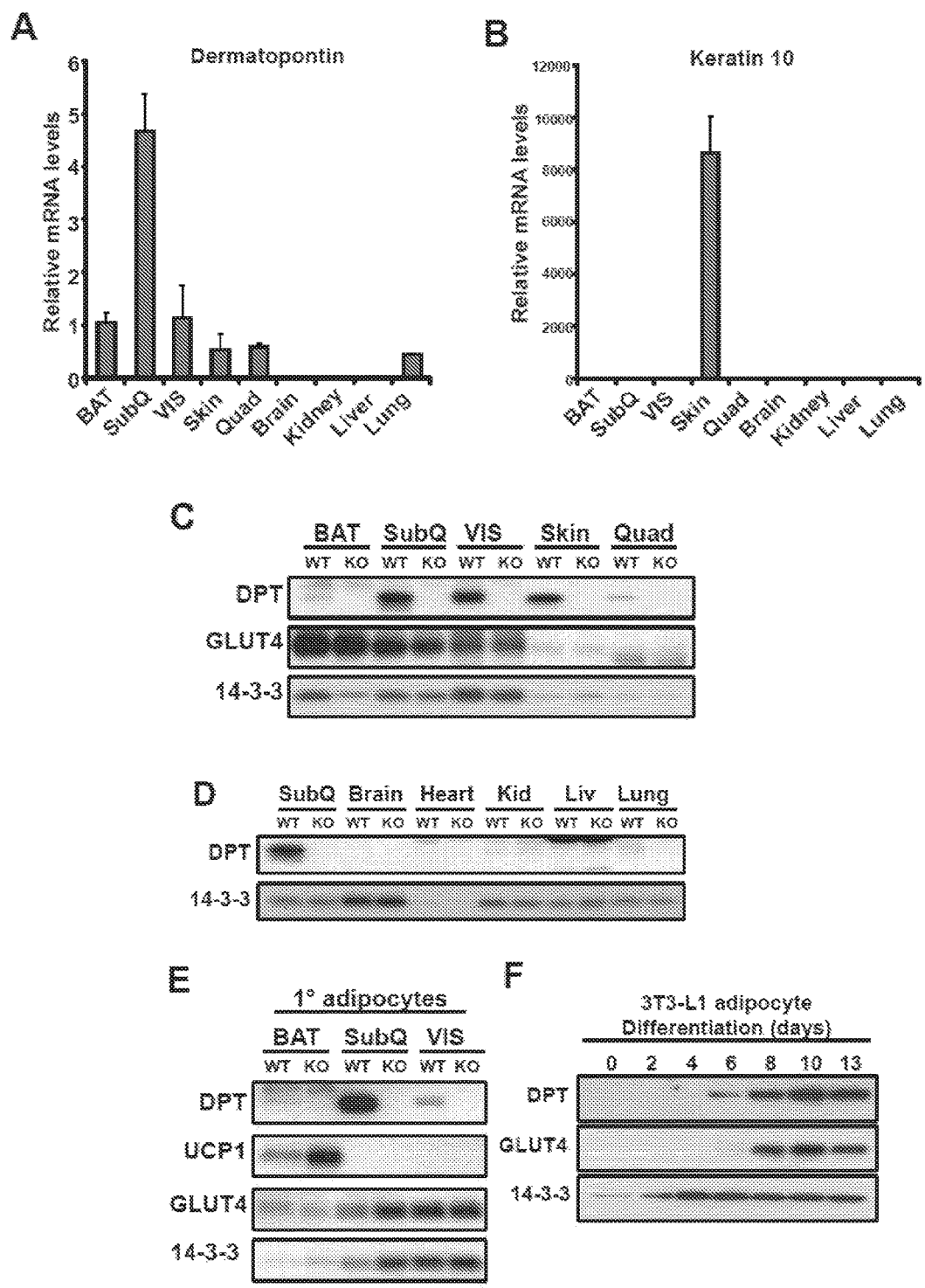
FIG. 3 shows data showing that dermatopontin is highly expressed in subcutaneous fat and is secreted by adipocytes. Relative mRNA levels of dermatopontin, using keratin 10 (a mature skin marker) as a positive control, are shown in the column graphs of A) and B), respectively. A) shows that the highest expression of dermatopontin in present in subcutaneous tissue, whereby B) shows the expression of keratin 10 (skin marker, positive control) being limited to skin only. C) and D) show western blot images of cell lysate isolated from various tissues of wild-types and dermatopontin knockout (DPT KO) mice, using antibodies against dermatopontin (DPT), glucose transporter type 4 (GLUT4) and the protein 14-3-3. This data shows the expression of dermatopontin to be localised in the same samples as quantitatively determined in A), also confirming that dermatopontin expression has been effectively prevented in the dermatopontin knock-out mouse. E) shows a western blot of lysates from primary adipocytes from the three different fat depots, which were immunoblotted using antibodies against dermatopontin (DPT), brown adipose tissue marker uncoupling protein 1 (UCP1), adipose tissue marker glucose transporter type 4 (GLUT4) and ubiquitous protein 14-3-3, whereby UCP1 is provided as an identity control confirming that the isolated adipose depot comprise brown adipose tissue. GLUT4 is highly expressed in all adipose tissues and therefore acts as a positive control that the isolated tissue is adipose tissue. Ubiquitous protein 14-3-3 serves as a general protein marker. F) shows an image of a western blot of a time course differentiation of 3T3-L1 fibroblast to adipocytes. Cell lysates were harvested at the indicated time point and immunoblotted with antibodies against dermatopontin (DPT), glucose transporter type 4 (GLUT4) and the protein 14-3-3. The data shown here shows that the level of DPT present in the adipocyte cells increases with differentiation of the cells over time. G) shows a western blot of serum samples isolated from wild-type or dermatopontin knockout (DPT KO mice), which were immunoblotted with antibodies against dermatopontin (DPT). The non-specific bands shown here act as a loading control. H) shows an image showing the results of a western blot analysis of 3T3-L1 adipocytes cells expressing dermatopontin (DPT)-myc, which were incubated in serum free media. The media and cell lysate were harvested at the indicated time points and immunoblotted for myc and fatty acid binding protein 4 (FABP4, a lipid transport protein in adipocytes). This data here shows that dermatopontin, while also being present in the cell, is mainly secreted into the media, while FABP4 is present predominantly in cell lysate, showing that FABP4 is not secreted out of the cell. I) shows a western blot of 3T3-L1 adipocytes cells expressing DPT-myc, which were treated with the indicated compounds for 6 hours. Brefeldin A (BFA) is a compound that inhibits endoplasmic reticulum and Golgi function. Insulin (Ins) is a hormone that elicits many signalling events and have been demonstrated to induce many secretory events in adipocytes. Cell lysates and media were harvested and immunoblotted using antibodies against myc, adiponectin, fatty acid binding protein 4 (FABP4, a lipid transport protein in adipocytes) and protein kinase b (AKT). Adiponectin and FABP4 both serve as control proteins for the respective treatments performed in this experiment. Adiponectin is a known secreted factor from adipocytes that is sensitive to brefeldin A (BFA) treatment (that is, in the presence of BFA, adiponectin is not secreted into the media). The presence or absence of adiponectin acts as a control for the effect of BFA on a known secreted protein. Thus, the BFA treatment is also shown to work for dermatopontin, which is also a secreted protein. FABP4 secretion is known to be unaffected by BFA and therefore acts as a negative control for the BFA treatment. Insulin is a known trigger of adiponectin secretion, which was demonstrated in the present experiment. It can be seen that the levels of dermatopontin do not change in the presence of insulin. Protein kinase b (AKT) acts as a loading control for the total cell lysate, and also acts as a control showing that the cell culture media does not contain dead cells debris. In the event that cell debris is present in the cell culture media, AKT would be detectable in the western blot analysis for the media panel.
Figure 3:
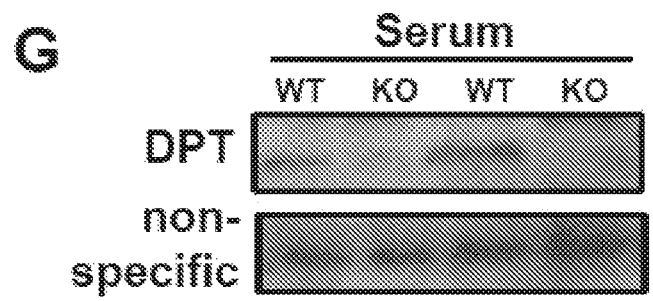
Figure 3:
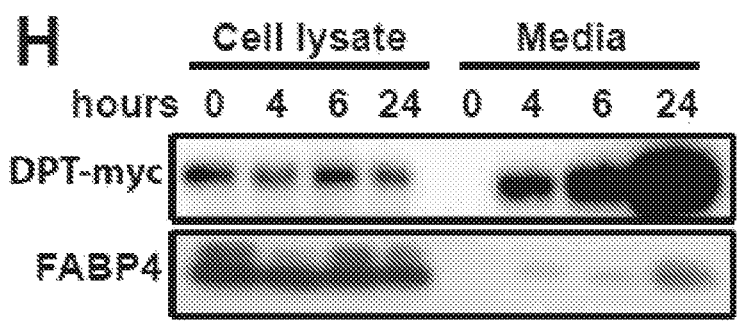
Figure 3:
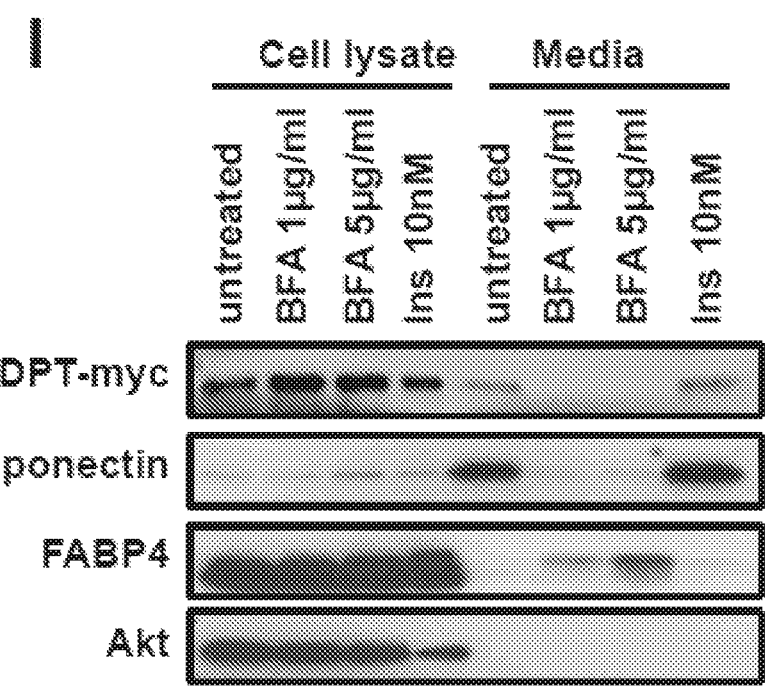

To explore the role of dermatopontin (DPT) in tissues, firstly the mRNA expression of dermatopontin in a panel of different tissues isolated from mouse was verified. Although dermatopontin was first found and isolated in skin, the mRNA expression data shows that dermatopontin transcripts are mostly expressed in subcutaneous fat depots, followed by visceral fat, skin, brown adipose tissue and muscle (FIG. 3A). The isolation method of skin was verified by determining the level of a mature skin marker, keratin 10, as shown in FIG. 3B. Given that skin isolates contain a layer of subcutaneous fat, it is indirectly shown that dermatopontin is highly expressed in the subcutaneous fat. Next, the protein expression of dermatopontin in various tissues was determined using specific antibodies generated against dermatopontin. A whole body dermatopontin knockout mouse line was used as a negative control. Similar to the dermatopontin mRNA expression, the dermatopontin protein levels were shown to be highly expressed in subcutaneous fat, follow by visceral fat, skin, muscle and brown adipose depot (FIGS. 3C &D). The remaining tissue types showed a minimal amount of dermatopontin expression to be present (FIG. 3D).

To further determine if dermatopontin is indeed present in the adipocytes, and not in other cell types within the adipose depot, primary adipocytes from adipose tissue were isolated. Dermatopontin was found to be highly expressed in the primary adipocytes, especially in the primary subcutaneous adipocytes (FIG. 3E). Use was made of a commonly used adipocyte cell line, 3T3-L1, to determine dermatopontin levels during the course of the differentiation of 3T3-L1 fibroblasts to adipocytes. Dermatopontin levels increased with differentiation, similar to that of adipocyte marker glucose transporter type 4 (GLUT4; FIG. 3F). This data shows that dermatopontin is highly expressed in adipose depots, more specifically in adipocytes.

Given that mammalian dermatopontin has a highly conserved, 18-amino acid classical secretory signal at its N-terminus and that it does not have any transmembrane domain based on prediction (data not shown), the secretion of dermatopontin from cells was analysed. A C-terminus myc epitope-tagged dermatopontin protein was used to perform a time course assay for the secretion of the same. The dermatopontin-myc fusion protein (DPT-myc) was observed in the media within 4 hours of serum-free media replacement, thus showing that the cells stably express the dermatopontin-myc fusion protein (DPT-myc), which is secreted into the media. The dermatopontin-myc fusion protein (DPT-myc) was abundant in the media after 24 hours (FIG. 3H). Treatment of cells with an endoplasmic reticulum (ER)/Golgi inhibitor, brefeldin A, blocked secretion of DPT-myc, similar to that of another known secreted protein, adiponectin (FIG. 3I). Furthermore, it was possible to detect endogenous dermatopontin in serum isolated from wild-type mice, but not in the serum from whole body dermatopontin knockout mice (FIG. 3G). Collectively, this data shows that dermatopontin is secreted from adipocytes via the classical ER-Golgi pathway.

Adipose and Circulating Dermatopontin Levels Correlated with Body Weight

Figure 4:
FIG. 4 illustrates data showing that dermatopontin (DPT) levels in two fat depots and serum correlate with the body weight of the mice. A) shows an image showing the result of a western blot of subcutaneous and visceral adipose tissue of CHOW, food restricted and high fat diet (HFD) mice, and the corresponding, resulting expression of dermatopontin (DPT) and heat-shock protein 90 (HSP90), respectively. It is shown that dermatopontin levels are higher when mice were on a high fat diet (HFD) and lower when the mice were food-restricted, with CHOW fed mice showing media levels of DPT. B) shows column graphs, representing a quantification of the data shown in A). C) shows line graph correlations of the subcutaneous (left panel), visceral (center panel) fat and serum (right panel) dermatopontin (DPT) levels to the respective body weights. In this figure, *p<0.05, p<0.01 and *p<0.005.
Figure 4:
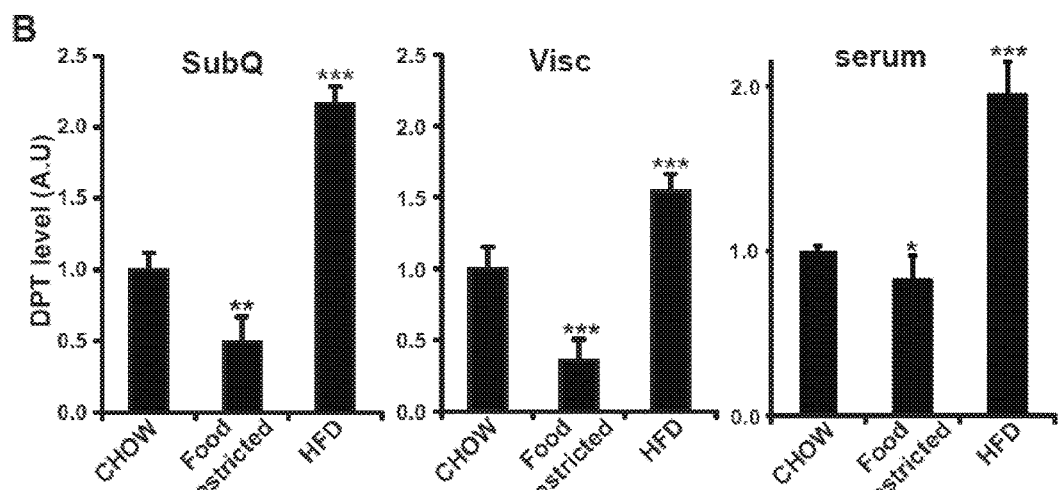
Figure 4:
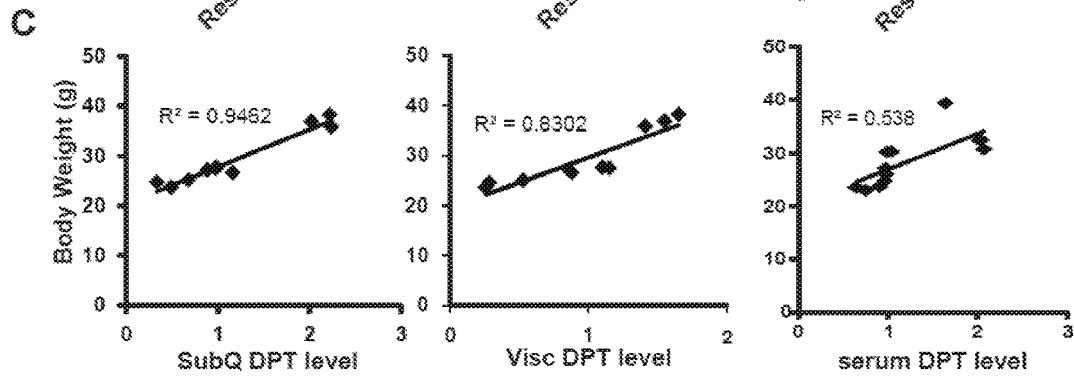

Next step was to determine if the relationship between the amount of dermatopontin found in circulation and the subject's weight gain. For this purpose, 3 groups of mice were designed as follows: one group of mice were fed a standard CHOW diet, the second group of mice were fed a high fat diet (HFD) and the third group of mice were fed a high fat diet but was food restricted to the point where these mice lost more weight compared to the CHOW fed mice (FR). Subcutaneous adipose and visceral adipose were isolated from each of these mice and immunoblotted for dermatopontin. In both types of fat depots (subcutaneous and visceral), the dermatopontin levels were high when mice were on a high fat diet (HFD) and lower when the mice were food-restricted (FR) (FIGS. 4A and 4B). When plotted against the body weight of each individual mouse, dermatopontin levels positively correlated with the weight of the respective mouse (FIG. 4C). Circulating dermatopontin levels in serum showed a similar trend as seen with adipose dermatopontin levels, despite a lower coefficient of determination $R^2$ in terms of correlation of the data points shown to a theoretical regression line (FIG. 4A to C).

Figure 5:
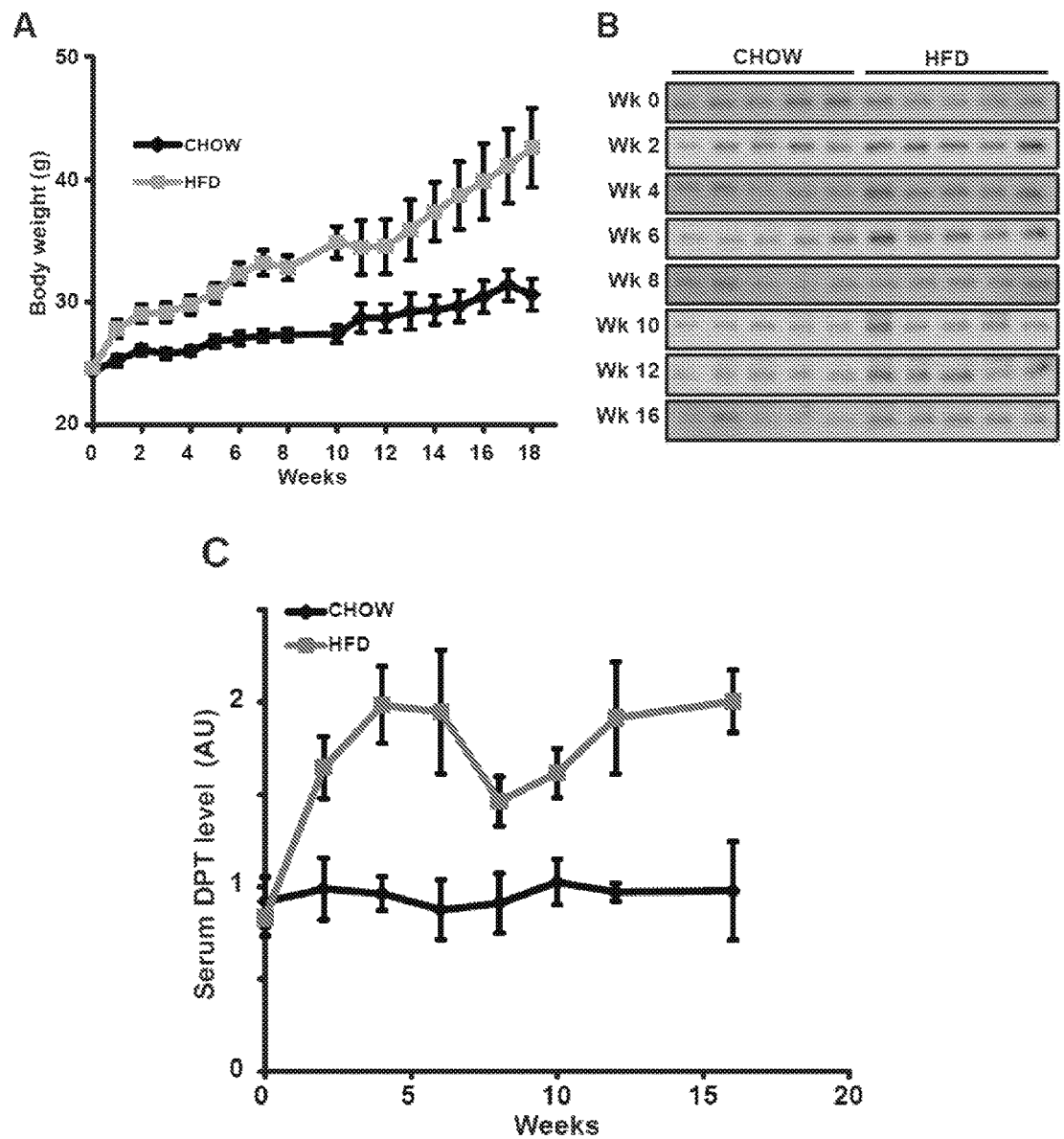
FIG. 5 shows that dermatopontin (DPT) levels in the serum increase over time in mice fed a high fat diet. A) is a line graph showing an increase in body weight of mice that were fed standard CHOW diet or a high fat diet (HFD), respectively. The HFD fed mice showed a higher weight gain in the same period of time compared to CHOW fed mice. B) shows a western blot of the serum of mice bleed at the indicated week and immunoblotted for dermatopontin (DPT), showing that the amount of DPT detected in HFD mice is increased compared to the DPT levels detected for CHOW fed mice. C) shows a line chart showing the quantification of the dermatopontin (DPT) levels previously shown in B). *p<0.05, p<0.01, *p<0.005.

To determine the temporal effect of diet induced weight gain due to dermatopontin, circulating dermatopontin levels were analysed over time. When mice are on a high fat diet (HFD), their dermatopontin levels were elevated within 2 weeks from the onset of the HFD. This increased level was maintained at a higher level than the CHOW-fed group (FIG. 5A to C), showing that a rise in dermatopontin level in circulation is an early marker for diet-induced weight gain in mice.

Figure 6:
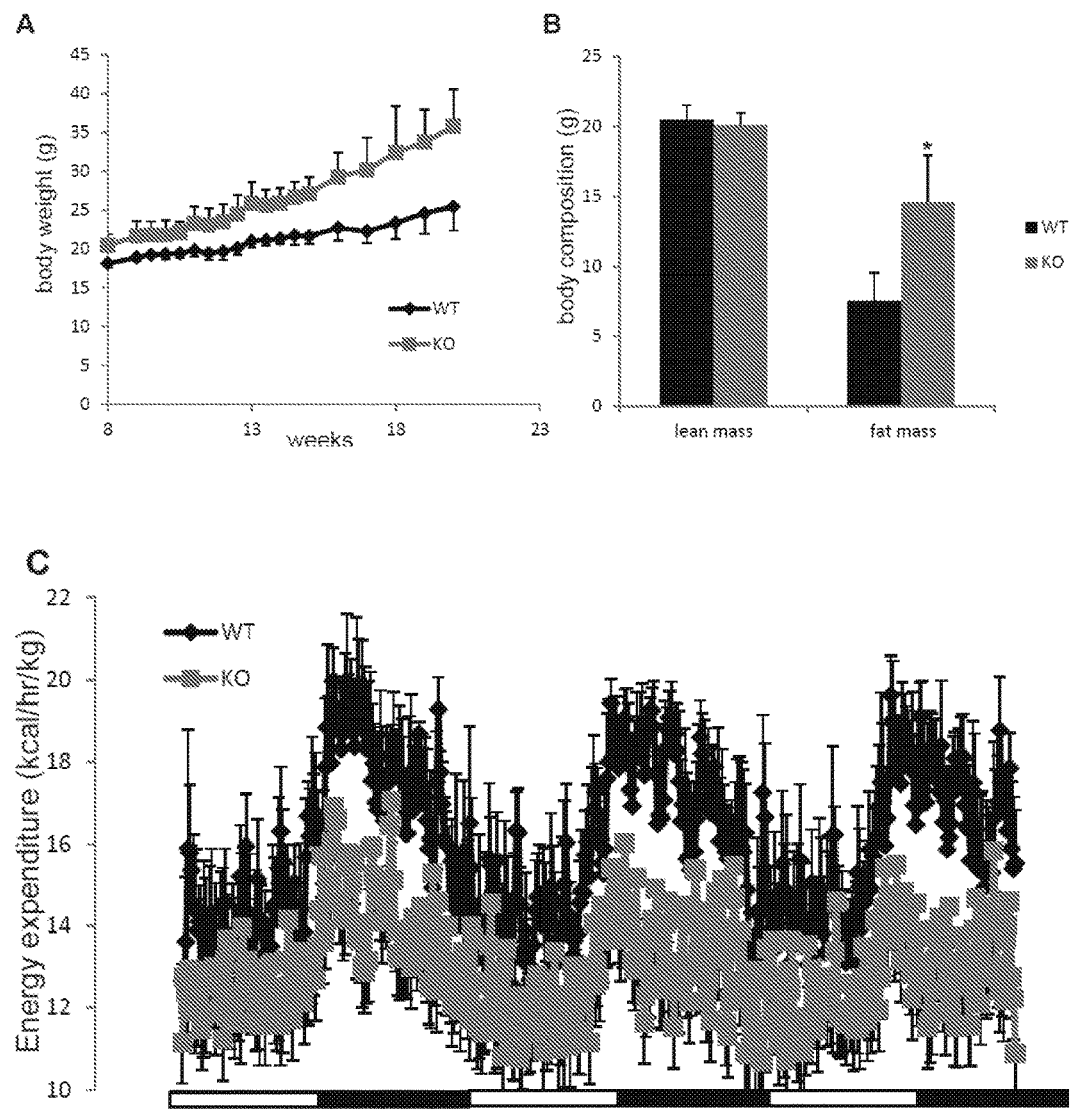
FIG. 6 shows data showing that a whole body, dermatopontin knockout mouse line has increased body weight and reduced energy expenditure when place on a high fat diet. A) shows a line graph depicting the body weight of wild-type (WT) mice versus dermatopontin knockout (KO) mice, showing that the KO mice exhibited a higher increase in body weight compared to WT mice. B) shows column charts showing the distribution of lean and fat mass of wild-type versus dermatopontin knockout (DPT KO) mice. This graph shows that amount of lean mass present in the mouse is similar between DPT KO mice and WT mice, but that DPT KO mice exhibit a higher fat mass compared to WT mice. C) shows a line graph depicting the energy expenditure in light (white horizontal bars on the y-axis) and dark (black horizontal bars on the y-axis) of wildtype (WT) versus dermatopontin knockout (DPT KO) mice. This graph shows that overall, the energy expenditure of DPT KO mice was lower than the energy expenditure of WT mice. D) shows a column graph depicting the average energy expenditure of the mice shown previously in C), that is the quantification of the data provided in C). For FIG. 6, the following criteria apply: n=4 per group, $*p<0.05$ and $***p<0.005$.
Figure 6:
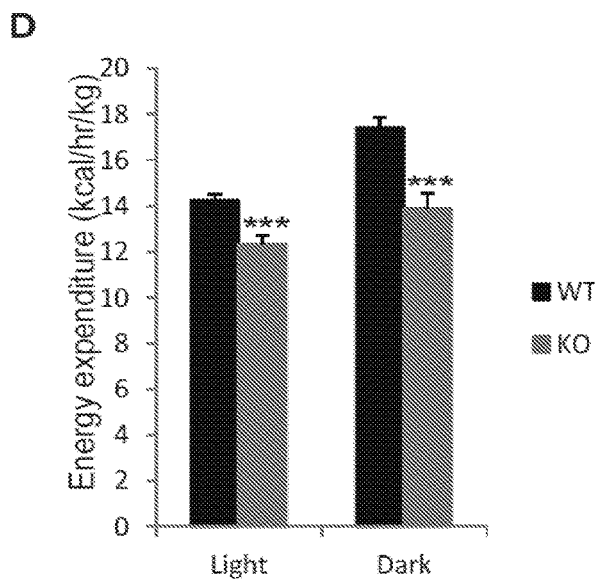
Figure 7:
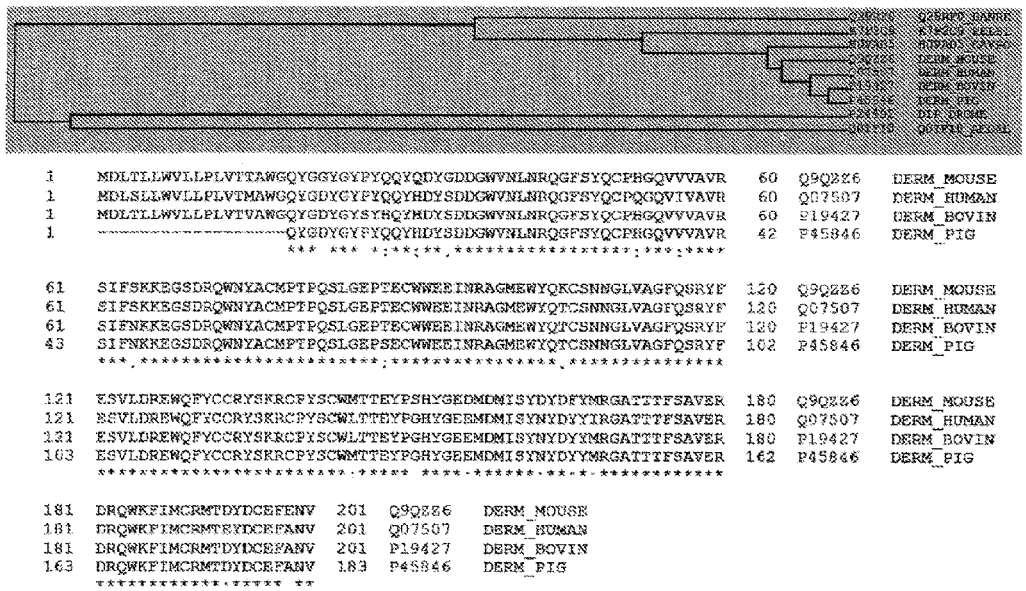
FIG. 7 shows an alignment analysis of human, (SEQ ID NO: 1), murine (SEQ ID NO: 3), bovine (SEQ ID NO: 2), and porcine (SEQ ID NO: 4) dermatopontin, thereby showing how closely related the protein sequences are to each other. The murine, bovine, human and porcine dermatopontin sequences were compared using a standard protein alignment program, thereby showing that the sequence is highly conserved across various species.

Recombinant Dermatopontin Reduces Weight Gain Induced by a Diet High in Fat and Increases Energy Expenditure Given that dermatopontin is secreted from adipose tissue and found in circulation, the next step was to determine the role of dermatopontin by injecting dermatopontin into mice and determine its effect. Recombinant dermatopontin (rDPT; FIG. 2A) or the vehicle control was injected into C57BL6 mice on a standard CHOW diet 3 times per week for two weeks at 2 mg/kg body weight. This was done for two weeks prior to a change in diet to a diet high in fat (high fat diet; HFD), and the injection regimen continued. At week 6 after injection, a significant reduction of weight gain was observed in the recombinant dermatopontin injected group (FIG. 2B). This reduction in weight is mostly due to a loss in fat mass. Glucose tolerance tests (GTT) revealed that the recombinant dermatopontin injected group had improved glucose clearance (FIGS. 2D &E). This increase in glucose clearance is attributed to increases in insulin sensitivity of the peripheral tissue based on the results of the insulin tolerance test (ITT; FIGS. 2F &G). Indirect calorimetry analysis revealed that recombinant dermatopontin injected mice have an increased energy expenditure, both during the day and night cycles (FIGS. 2H &I), without affecting parameters, for example such as food and water intake, and movement (FIG. 8). Collectively, this data shows that recombinant dermatopontin injections have an overall beneficial effect on subject metabolism. Specifically, recombinant dermatopontin can improve glucose clearance during a glucose challenge. This is attributed to higher resting (day time) energy expenditure and also increased active (night time) energy expenditure, which contributes to the improvement of peripheral tissue insulin sensitivity.] It is also shown that a whole-body dermatopontin knockout mouse line is more sensitive to diet-induced weight gain (FIG. 6A).

To verify the biological effect of dermatopontin, a whole-body DPT knockout (KO) mouse line was analysed. Wild-type or dermatopontin knockout mice (DPT KO) were fed a high fat diet. The dermatopontin knockout mice showed an increase in weight when put on the high fat diet (HFD, FIG. 6A), mainly due to the increase in fat mass (FIG. 6B). Indirect calorimetry analysis showed that dermatopontin knockout mice have lower energy expenditure, both during the day and night times (FIGS. 6C and D) without affecting any of the other parameters examined (data not shown). The data on dermatopontin knockout mice and the effect of recombinant dermatopontin confirmed that dermatopontin affects the basal energy expenditure, which has also been shown in FIG. 2H, as previously discussed.

Correlation Studies

Eight week old male C57BL/6J mice were given standard chow or high fat (60% kcal fat) diet for 8 weeks. Body weight measurements were performed every week. On the $9^{th}$ week of the diet, the mice on a high fat diet were spilt into two groups: the first continued on a high fat diet, whereas the second were given 16.5% of their daily intake once in the morning and once in the evening (total 33% of normal intake; restricted intake). 10 days later, mice from all 3 groups (mice on standard CHOW, mice on HFD and mice on restricted HFD) were sacrificed via cervical dislocation. Blood was taken via cardiac puncture and the serum was obtained after clotting the blood on ice for 1 hour. A separate cohort of mice was put on CHOW or a high fat diet (HFD) and blood were obtained via tail bleeding every 2 weeks to detect dermatopontin. Visceral fat was obtained from the epididymal depot, and subcutaneous fat was obtained from the posterior adipose depot. Western blot analysis was performed as follows: tissues were homogenised in Radio-Immunoprecipitation Assay (RIPA) buffer with protease inhibitors, and resulting protein concentration was quantified using a bicinchoninic acid assay (BCA) assay. Similar methods for isolating and determination protein concentration known in the art may also be utilised. 20 μg of tissue lysate or 1 μl of serum were mixed with sample loading buffer and were loaded onto a polyacrylamide gel and were separated by sodium dodecyl sulfate-polyacrylamide gel electrophoresis (SDS-PAGE). After transferring proteins to polyvinylidene difluoride membranes, the membranes were blocked (5% skim milk in TBS-Tween) and subsequently immunoblotted with antibodies against dermatopontin or heat shock protein 90 (HSP90) overnight at 4° C. The antibodies were diluted at a ratio of 1:1000 in 2% BSA TBS-Tween). After incubation, the membranes were washed and incubated with horseradish peroxidase-labelled secondary antibodies and then detected by chemiluminescent substrate incubation, followed by film exposure. The resulting Western blots were quantified using the ImageJ program. Correlation graphs and $R^2$ were plotted and calculated using Microsoft Excel.

Recombinant Dermatopontin Studies

Eight week old male C57BL/6J mice were given standard chow diet for two weeks before injected with PBS (control vehicle) or recombinant dermatopontin at 2 mg/kg body weight 3 times a week for the two weeks indicated above. Two weeks after the first recombinant dermatopontin injection, mice were placed on high fat diet. Intraperitoneal glucose tolerance tests (GTTs) were performed on mice following a 6 hour fast. Mice were injected with a 20% (w/v) glucose solution at a final dose of 2 g/kg. Blood glucose was measured by sampling blood from the tail tip at the indicated time points with an Accu-Check II glucometer (FIG. 2D). Intraperitoneal insulin tolerance tests (ITT) were performed on mice following a 2 hour fast. Mice were injected with 2 U insulin per kg body weight. Blood glucose was measured according to that of glucose tolerance test (GTT) as stated above. Energy expenditure, resting respiratory rate, food and water intake, movement, oxygen and carbon dioxide measurements were performed using Columbus Instruments Comprehensive Lab Animal Monitoring System (CLAMS). Lean mass and fat mass composition was measured using Echo magnetic resonance imaging (MRI).

TABLE 1

List of sequences

| SEQ ID NO: | Name | Sequence |
|---|---|---|
| 1 | Recombinant dermatopontin (human; protein) | MDLSLLWVLLPLVTMAWGQYGDYGYPYQQYHDYSDDGWV NLNRQGFSYQCPQGQVIVAVRSIFSKKEGSDRQWNYACMPTP QSLGEPTECWWEEINRAGMEWYQTCSNNGLVAGFQSRYFES VLDREWQFYCCRYSKRCPYSCWLTTEYPGHYGEEMDMISYN YDYYIRGATTTFSAVERDRQWKFIMCRMTEYDCEFANV |
| 2 | Recombinant dermatopontin (bovine; protein) | MDLTLLWVLLPLVTVAWGQYGDYGYSYHQYHDYSDDGWV NLNRQGFSYQCPHGQVVVAVRSIFNKKEGSDRQWNYACMPT PQSLGEPTECWWEEINRAGMEWYQTCSNNGLVAGFQSRYFE SVLDREWQFYCCRYSKRCPYSCWLTTEYPGHYGEEMDMISY NYDYYMRGATTTFSAVERDRQWKFIMCRMTDYDCEFANV |
| 3 | Recombinant dermatopontin (murine; protein) | MDLTLLWVLLPLVTTAWGQYGGYGYPYQQYQDYGDDGWV NLNRQGFSYQCPHGQVVVAVRSIFSKKEGSDRQWNYACMPT PQSLGEPTECWWEEINRAGMEWYQKCSNNGLVAGFQSRYFE SVLDREWQFYCCRYSKRCPYSCWMTTEYPSHYGEDMDMISY DYDFYMRGATTTFSAVERDRQWKFIMCRMTDYDCEFENV |
| 4 | Recombinant dermatopontin (porcine; protein) | QYGDYGYPYQQYHDYSDDGWVNLNRQGFSYQCPHGQVVV AVRSIFNKKEGSDRQWNYACMPTPQSLGEPSECWWEEINRAG MEWYQTCSNNGLVAGFQSRYFESVLDREWQFYCCRYSKRCP YSCWMTTEYPGHYGEEMDMISYNYDYYMRGATTTFSAVER DRQWKFIMCRMTDYDCEFANV |
| 5 | Human dermatopontin (DPT) nucleic acid sequence used to generate recombinant DPT constructs | atggacctcagtcttctctgggtacttctgcccctagtcaccatggcctggggccagtatggcgatt atggatacccataccagcagtatcatgactacagcgatgatgggtgggtgaatttgaaccggcaa ggcttcagctaccagtgtccccaggggcaggtgatagtggccgtgaggagcatcttcagcaaga aggaaggttcgacagacaatggaactacgcctgcatgcccacgccacagagcctcggggaac ccacggagtgctggtgggaggagatcaacagggctggcatggaatggtaccagacgtgctcca acaatgggctggtggcaggattccagagccgctacttcgagtcagtgctggatcgggagtggca gttttactgagtcgctacagcaagaggtgcccatattcctgctggctaacaatagaatatccaggtc actatggtgaggaaatggacatgatttcctacaattatgattactatatccgaggagcaacaaccact ttctctgcagtggaaagggatcgccagtggaagttcataatgtgccggatgactgaatacgactgt gaatttgcaaatgtttag |
| 6 | Conserved N-terminal secretory sequence (human) | MDLSLLWVLLPLVTMAWG |
| 7 | Conserved N-terminal secretory sequence (bovine) | MDLTLLWVLLPLVTVAWG |
| 8 | Conserved N-terminal secretory sequence (murine) | MDLTLLWVLLPLVTTAWG |
| 9 | Nuclear localisation sequence of nucleoplasmin | AVKRPAATKKAGQAKKKLD |
| 10 | Nuclear localisation sequence of c-myc | PAAKRVKLD |
| 11 | His-tagged recombinant dermatopontin (rDPT-His)(DNA) | atggacctcagtcttctctgggtacttctgcccctagtcaccatggcctggggccagtatggcgatt atggatacccataccagcagtatcatgactacagcgatgatgggtgggtgaatttgaaccggcaa ggcttcagctaccagtgtccccaggggcaggtgatagtggccgtgaggagcatcttcagcaaga aggaaggttcgacagacaatggaactacgcctgcatgcccacgccacagagcctcggggaac ccacggagtgctggtgggaggagatcaacagggctggcatggaatggtaccagacgtgctcca acaatgggctggtggcaggattccagagccgctacttcgagtcagtgctggatcgggagtggca gttttactgagtcgctacagcaagaggtgcccatattcctgctggctaacaatagaatatccaggtc actatggtgaggaaatggacatgatttcctacaattatgattactatatccgaggagcaacaaccact ttctctgcagtggaaagggatcgccagtggaagttcataatgtgccggatgactgaatacgactgt gaatttgcaaatgttcatcatcatcatcatcattga |
| 12 | His-tagged recombinant dermatopontin (rDPT-His) (Protein) | MDLSLLWVLLPLVTMAWGQYGDYGYPYQQYHDYSDDGWV NLNRQGFSYQCPQGQVIVAVRSIFSKKEGSDRQWNYACMPTP QSLGEPTECWWEEINRAGMEWYQTCSNNGLVAGFQSRYFES VLDREWQFYCCRYSKRCPYSCWLTTEYPGHYGEEMDMISYN YDYYIRGATTTFSAVERDRQWKFIMCRMTEYDCEFANVHHH HHH |

What is claimed is:

1. A method of treating a metabolic disease in a subject, wherein the method comprises administering a recombinant dermatopontin to a subject, wherein the metabolic disease is selected from the group consisting of weight gain, diet-induced weight gain, obesity, morbid obesity, metabolic syndrome, insulin resistance, type I diabetes, type II diabetes and cardiovascular disease, wherein the recombinant dermatopontin comprises the sequence selected from the group consisting of SEQ ID NO: 1, SEQ ID NO: 2, SEQ ID NO: 3 SEQ ID NO: 4.

2. The method of claim 1, wherein the recombinant dermatopontin is of human, bovine, porcine or murine origin.

3. The method of claim 1, wherein the recombinant dermatopontin comprises SEQ ID NO: 1.

4. The method of claim 1, wherein the recombinant dermatopontin is post-translationally modified.

5. The method of claim 1, wherein the recombinant dermatopontin is modified at its C-terminus or N-terminus.

6. The method of claim 5, wherein the recombinant dermatopontin comprises a detection and/or characterization tag.

7. The method of claim 1, wherein the recombinant dermatopontin is encoded by the nucleic acid sequence consisting of SEQ ID NO: 5.

8. The method of claim 1, further comprising administering the recombinant dermatopontin with at least one or two or more therapeutic agents.

9. The method of claim 8, wherein the administration is simultaneous, separately or sequentially.

10. The method of claim 1, wherein administration of the recombinant dermatopontin is in an amount of between 0.1 mg/kg and 10 mg/kg.

11. The method of claim 1, wherein administration of the recombinant dermatopontin is carried out daily, weekly, twice a week, three times a week, every two weeks or monthly.

12. The method of claim 1, where the subject is human.

* * * * *